United States Patent [19]

Suzuki et al.

[11] Patent Number: 4,583,525
[45] Date of Patent: Apr. 22, 1986

[54] ARTIFICIAL HEART DRIVING APPARATUS

[75] Inventors: Akira Suzuki, Nishio; Takeharu Oumi, Tokyo; Sanshiro Takamiya, Nagoya; Hideo Nakazawa, Saitama, all of Japan

[73] Assignee: Aisin Seiki K.K., Aichi, Japan

[21] Appl. No.: 749,067

[22] Filed: Jun. 26, 1985

Related U.S. Application Data

[62] Division of Ser. No. 480,181, Mar. 28, 1983, Pat. No. 4,546,760.

[30] Foreign Application Priority Data

| Mar. 30, 1982 | [JP] | Japan | 57-52141 |
| Mar. 30, 1982 | [JP] | Japan | 57-52142 |
| Mar. 30, 1982 | [JP] | Japan | 57-52143 |
| Mar. 30, 1982 | [JP] | Japan | 57-45056 |
| Mar. 31, 1982 | [JP] | Japan | 57-52933 |

[51] Int. Cl.$^4$ .......................................... A61B 19/00
[52] U.S. Cl. ........................................ 128/1 D; 623/3
[58] Field of Search .............. 128/1 D; 3/1.7; 417/395

[56] References Cited

U.S. PATENT DOCUMENTS

| 3,234,932 | 2/1966 | Bird et al. | 128/204.19 |
| 3,465,746 | 9/1969 | Guarino | 128/1 D |
| 3,550,162 | 12/1970 | Huffman | 623/3 |
| 3,955,557 | 5/1976 | Takagi | 128/1 D |
| 3,966,358 | 6/1976 | Heimes et al. | 623/3 |

FOREIGN PATENT DOCUMENTS 0812295 3/1981 U.S.S.R. .................. 128/1 D

Primary Examiner—Kyle L. Howell
Assistant Examiner—Ruth S. Smith
Attorney, Agent, or Firm—Sughrue, Mion, Zinn Macpeak & Seas

[57] ABSTRACT

Positive pressure and negative pressure are alternately applied to artificial hearts so as to drive the same. Each of driving systems includes a pressure sensor, and a solenoid valve connected between a pressure source and an accumulator is controlled in its opening and closing in order that the detected pressure is made coincident with a set value. A pair of solenoid valves connected respectively to an output port of the accumulator in a positive pressure system and an output port of the accumulator in a negative pressure system are opened and closed, thereby to supply positive pressure air and negative pressure air to the artificial hearts alternately. There is also included a backup driving system, and upon receiving instruction for system switching, lamps are energized in due sequence so as to inform the operator of valves to be operated manually. Control of the solenoid valve is carried out by microcomputers, and a control board used for imparting instructions to the microcomputers includes a remote control unit which is connected to the apparatus body through a cable. The solenoid valves are installed within the corresponding accumulators.

13 Claims, 43 Drawing Figures

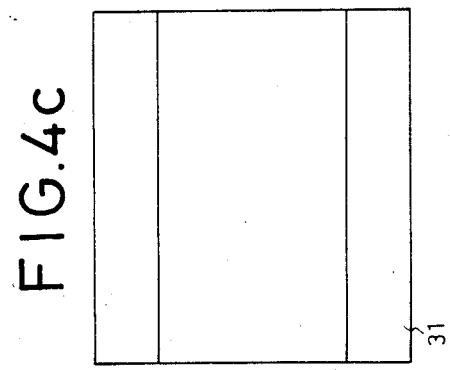
FIG.4c  FIG.4a
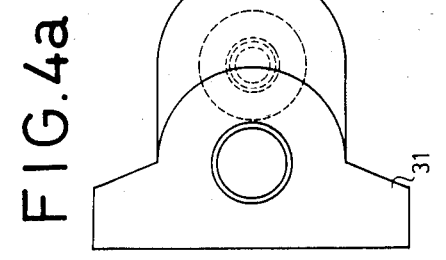
FIG.4b
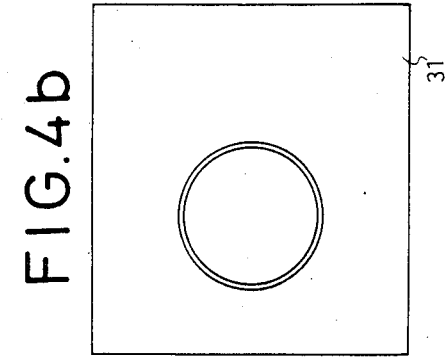
FIG.4d
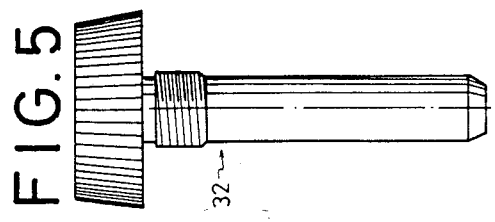
FIG.5
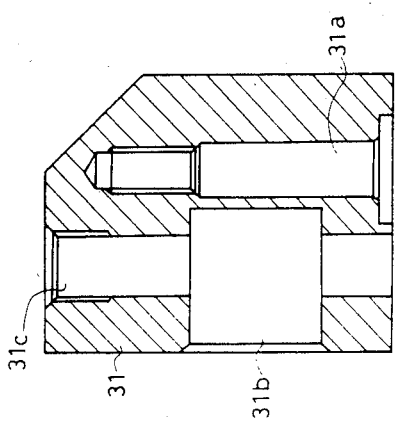

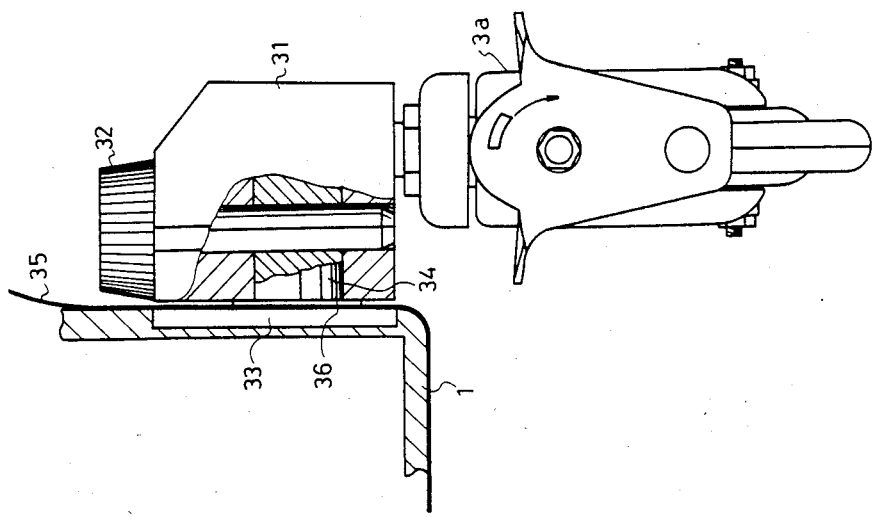
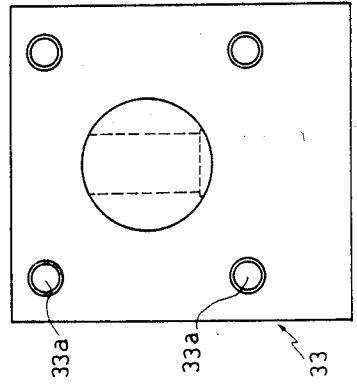
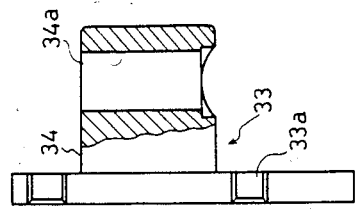

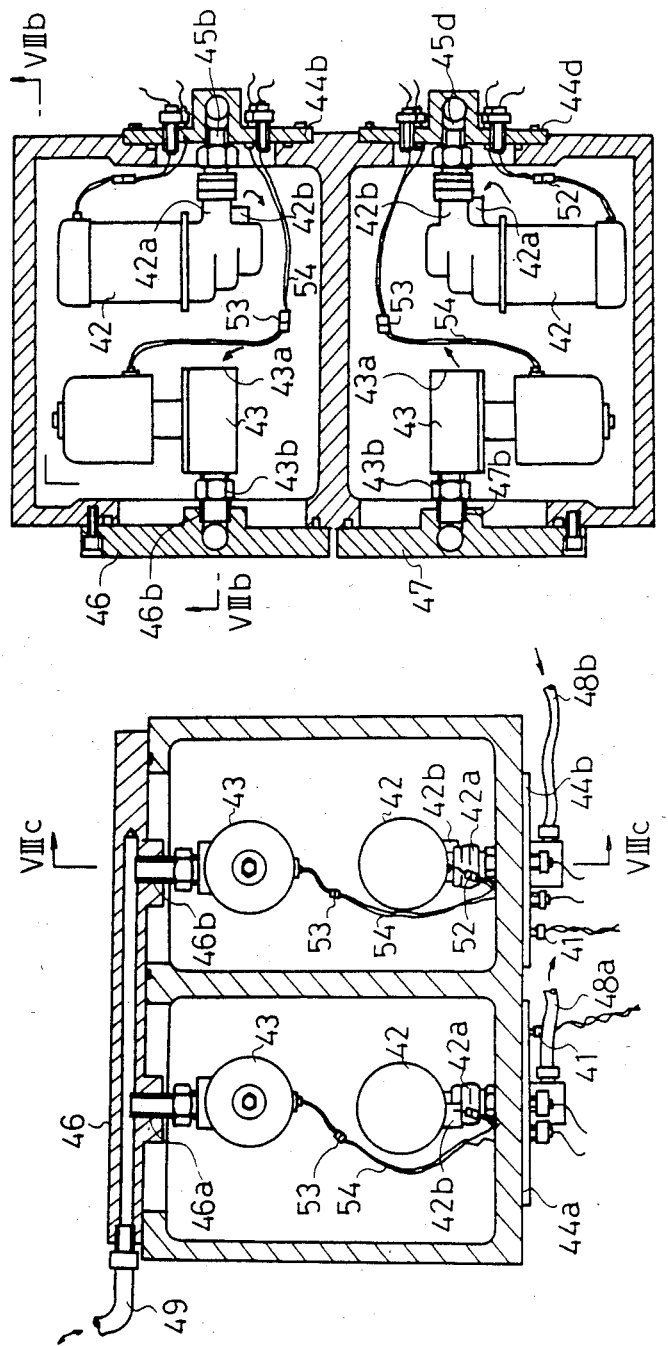

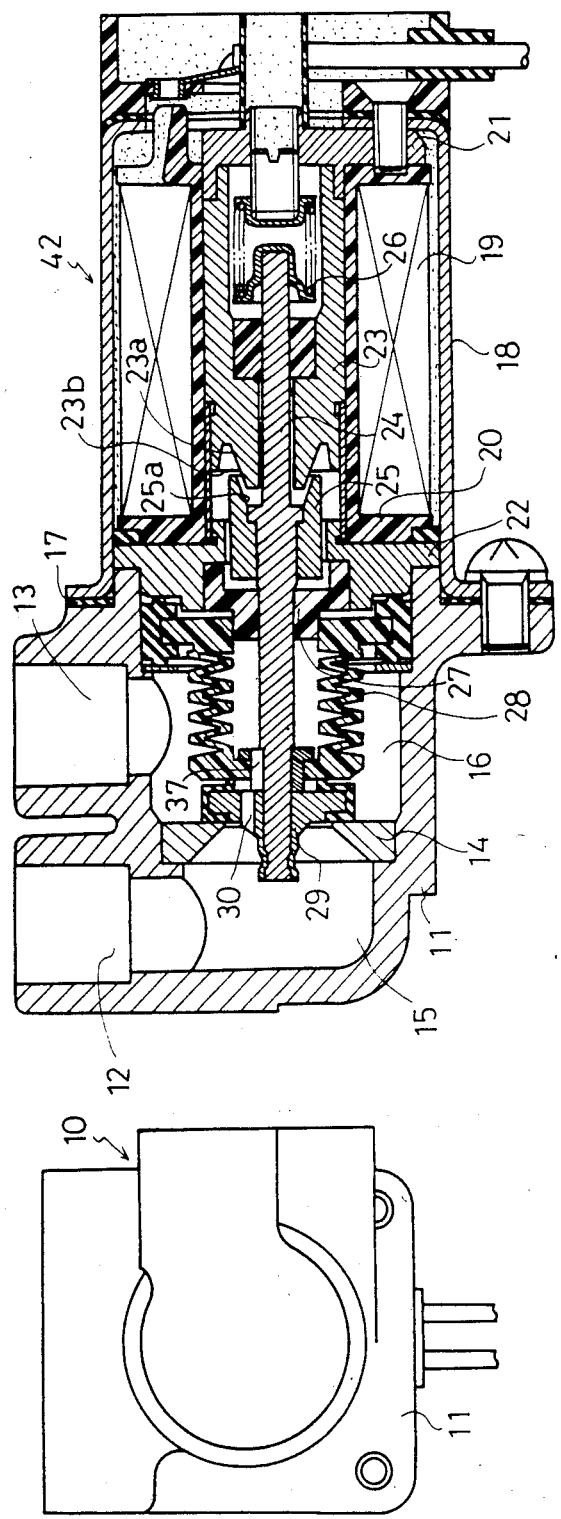

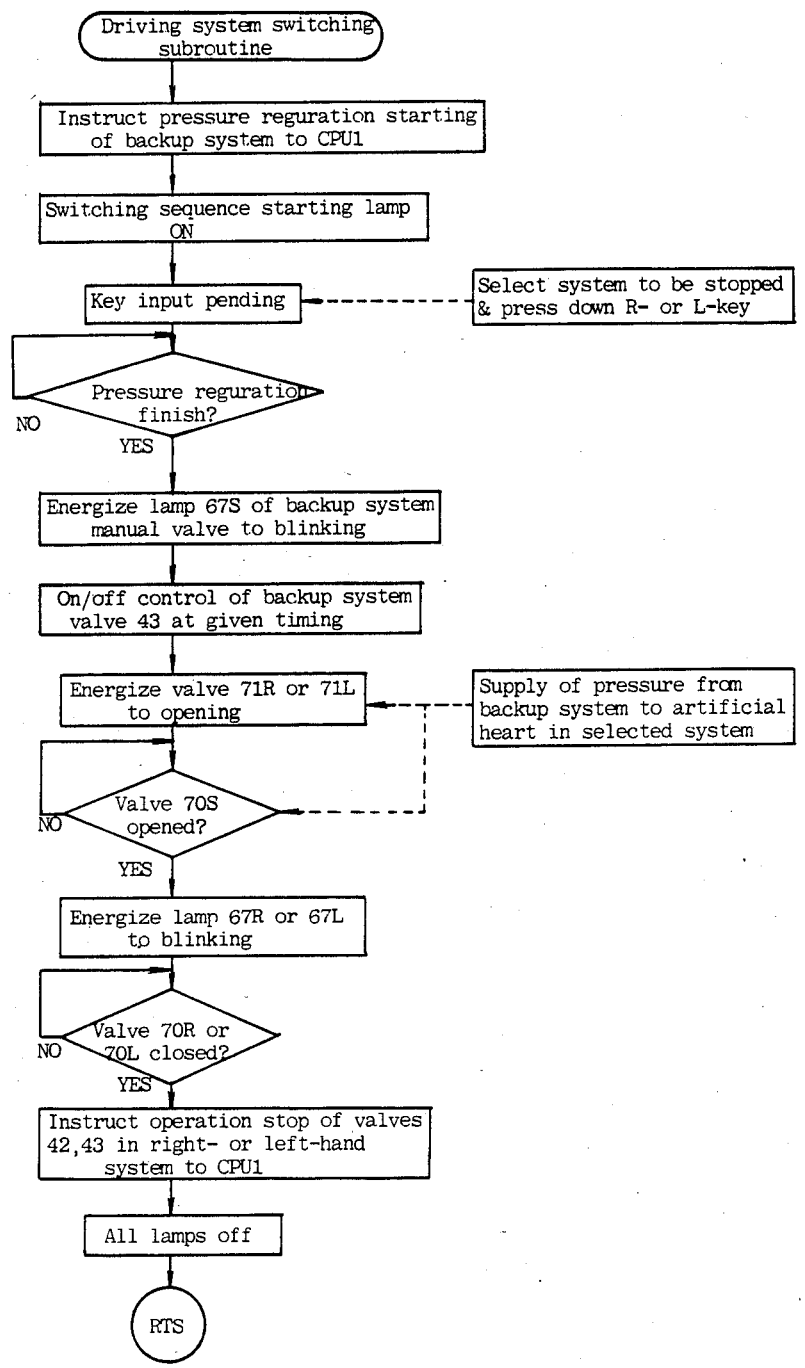

ARTIFICIAL HEART DRIVING APPARATUS

This is a division of application Ser. No. 480,181, filed Mar. 28, 1983, U.S. Pat. No. 4,546,760.

BACKGROUND OF THE INVENTION

The invention relates to an apparatus for driving an artificial heart, and more particularly to an artificial heart driving apparatus in which positive pressure and negative pressure are alternately applied to the artificial heart using a fluid such as air thereby to drive the same.

From the standpoint of safety, it is important for artificial hearts to be driven so that a pulsatory motion closely similar to pulsation of hearts in living bodies is imparted to blood. There are known a variety of artificial hearts, such as diaphragm type, sack type, piston type, which are usually driven by receiving the predetermined pressure from a fluid such as air. To drive those artififical hearts under the optimum conditions in accordance with the state of living bodies, it is essential to employ a driving apparatus which can generate correct pressure in accordance with the optimum conditions at proper timing. In other words, such a driving apparatus is preferable that is able to correctly and quickly set heart rate, positive pressure, negative pressure and duration or duty ratio of positive pressure and negative pressure applied to artificial hearts, etc. at the respective predetermined values.

In the prior artificial heart driving apparatus, mechanical pressure reducing valves or the like are used respectively in positive and negative pressure systems as means for attaining correct pressures. However, since outputs of both positive and negative pressure systems are interconnected to each other and hence negative pressure acts as a load for the positive pressure system, whereas positive pressure acts as a load for the negative pressure system, the foregoing artificial heart driving apparatus has a disadvantage such that adjustment of positive pressure varies a load for the positive pressure system and this results in changes of positive pressure, whereas adjustment of positive pressure varies a load for the negative pressure system and this results in changes of negative pressure. In the past, therefore, when adjusting pressures, the adjustment had to be carried out carefully even in the case of adjusting either one pressure in such a manner that a pair of two pressure reducing valves are operated at the same time while checking two levels of both pressures and one pressure is maintained at the predetermined value while updating a level of the other pressure. This results in the time-consuming pressure adjustment which also requires a great deal of skill. Moreover, the mechanical pressure reducing valves can not provide satisfactory performance, unless differential pressure between the inlet side and the outlet side is set to be relatively large. Thus, the pressure generated by a pressure source such as a compressor must be set as twice as that to be applied to artificial hearts. This leads to other disadvantages in that a large-sized pressure source is needed and levels of heating, noise, etc. are increased.

Meanwhile, the artificial heart driving apparatus of this kind is often used for a long period of time in succession. In such case, even if a part of the apparatus experiences trouble, the artificial heart can not be stopped in its driving. But when there occurs a trouble or anomaly, continued operation of the failed driving apparatus makes it impossible to drive the artificial heart under the best condition. Further, even in the case where no trouble or anomaly is observed from the outside, routine maintenance is necessary for internal parts of the apparatus. Accordingly, when carrying out maintenance, repairs, etc, up to now, another artificial heart driving apparatus is prepared and the previous driving apparatus is replaced by a new one by changing over a number of valves, cocks, etc. in the predetermined sequence in order that the artificial heart will never be stopped. But, when so many valves, cocks, etc. are changed over manually by operators, so it is impossible to absolutely eliminate a fear of switching those parts in wrong sequence. Also, at the time of exchanging the artificial heart driving apparatus, both apparatus are out of timing from each other in their drivings, whereby this exchange is accompanied with a highly possible danger.

In addition, the artificial heart driving apparatus of this kind must be equipped with a number of devices and units such as a compressor, vacuum pump, tank (accumulator), solenoid valve, control unit, etc., thus resulting in the large size. For example, artificial hearts are used as auxiliaries for the hearts of living bodies during a surgical operation, but the large-sized artificial heart driving apparatus can not be disposed near the operating table during an operation, because there are many doctors and operating equipment around the operating table. On the other hand, the artificial heart must be desirably varied in its heart rate, etc. in accordance with condition of the patient under an operation. Therefore, the prior artificial heart driving apparatus is placed at a position spaced from the operating table and then controlled by technical experts under instructions from the doctors. But, in order to drive the artificial heart under the optimum conditions, it is preferable that the driving apparatus is directly controlled by the doctors. Since the artificial heart driving apparatus in the past employs the mechanical pressure reducing valves or the like, it was difficult to realize such direct control and impossible to perform remote control.

There has been proposed another artificial heart driving apparatus in which solenoid valves to effect opening and closing control are respectively attached at the output end of a positive pressure system and the output end of a negative pressure system for switching positive and negative pressures to be applied to artificial hearts. In the apparatus of this kind, the solenoid valves are controlled by a control unit so that opening and closing are alternately switched at the predetermined timing in accordance with the preset heart rate. However, such artificial heart driving apparatus is disadvantageous in that occurrence of noise can not be avoided, because the solenoid valves are driven to be opened and closed alternately at all times. Sound-proofing covers or the like may be placed around the solenoid valves so as to suppress a level of noise, but this results in an increase of the size and cost and the apparatus becomes hard to move.

SUMMARY OF THE INVENTION

It is a first object of the invention to provide an artificial heart driving apparatus which can adjust both positive and negative pressures without affecting each other and which has good operability and high safety. Another object of the invention is to provide an artificial heart driving apparatus which can maintain both pressures at the predetermined values with high accuracy.

It is a second object of the invention to provide an artificial heart driving apparatus which can be subject to repairs of failed parts, maintenance, etc. without a need of preparing a backup artificial heart driving apparatus additionally. Another object of the invention is to provide an artificial heart driving apparatus which can drive artificial hearts continuously in the predetermined state even when carrying out repairs, maintenance, etc. and hence which has a high level of safety.

It is a third object of the invention to provide an artificial heart driving apparatus whose parameters can be directly varied by doctors. Another object of the invention is to provide an artificial heart driving apparatus which is simple in its operation and control.

Still another object of the invention is to provide an artificial heart driving apparatus which has a low level of noise.

To achieve the foregoing objects, according to the present invention, solenoid valves are respectively provided in a positive pressure system and a negative pressure system as means for attaining the predetermined levels of pressures, and those solenoid valves are controlled to be opened or closed in accordance with outputs from pressure detecting means which are connected to the corresponding systems, respectively, thereby to adjust both pressures. This pressure adjustment is carried out in such a manner that a ratio of opening time and closing time of each solenoid valve is varied so as to make the pressure detected by the pressure detecting means equal to the target pressure, or that each solenoid valve undergoes opening and closing control when pressure is varied to exceed the predetermined value. By so doing, both the positive and negative pressure systems are feedback-controlled independently from each other, whereby pressure of one system is automatically held at the predetermined value, while pressure of the other system is variably adjusted. Moreover, solenoid valves are used to control pressures, so that it becomes possible to electrically change values of all parameters for the artificial heart driving apparatus and this allows a control section for changing parameter values to be separated from a body of the artificial heart driving apparatus, thus permitting remote control. Since the artificial heart driving apparatus has the fairly large size and it can not be placed near the operating table during a surgical operation, there is a great deal demand for remote control.

In preferred embodiments of the invention, solenoid valves for adjusting pressure each include a fixed magnetic substance core and a movable magnetic substance core which are disposed along the axis of an electric coil, the movable magnetic substance core being movable in the axial direction with respect to the fixed magnetic substance core. The solenoid valves of this kind have good response performance and hence permit pressure control with high accuracy.

Further, in a preferred embodiment of the invention, a mechanical system comprising valves and other parts with relatively less reliability includes an additional backup system, and the mechanical system is switched to the backup system when carrying out repairs, maintenace, etc. At the time of this switching, solenoid valves in both the system to be stopped and the backup system are driven at the same time temporarily in synchronism with each other, and then the former system is stopped after completion of the predetermined switching operation. On this occasion, a control means is made to generate instructions such as the sequence of switchings in accordance with the predetermined key operation and valve operation. By so doing, it becomes possible to carry out repairs, maintenance, etc. without a need of using another artificial heart driving apparatus and also to minimize a fear of possible danger attendant upon switching of the systems, because there occurs no change in driving timing of the artificial heart at the time of such switching. Since the predetermined instructions are issued from the control means, a possibility of errors in operation by operators is also minimized.

Furthermore, in a preferred embodiment of the invention, instructions issued from the control means at the time of switching are made in the form of indications of the lights. With this, operators may change over valves, cocks, etc. in accordance with such indications of the lights, thus avoiding the occurrence of operational errors completely.

Other objects and features of the invention will become more apparent from a reading of the following description with reference to the drawings.

BRIEF DESCRIPTION OF THE DRAWINGS

FIG. 2b is an enlarged sectional view taken along the line II—II in FIG. 2a;

FIGS. 4a, 4b, 4c and 4d are a front view, left side view, right side view and a vertical sectional view of a casing which constitutes the caster, respectively;

FIG. 5 is a front view of a bolt used for fixing the caster;

FIGS. 6a and 6b are a front view and a side left view of a stand used for supporting the caster, respectively;

FIG. 7 is a partially broken front view showing the connection between the caster and a body of the artificial heart driving apparatus;

FIGS. 8a, 8b, 8c, 8d and 8e are a perspective view showing a tank unit within the artificial heart driving apparatus, a horizontal sectional view of the tank unit, a sectional view taken along the like VIIIc—VIIIc in FIG. 8b, a partial enlarged sectional view showing the connection between a terminal and a tank, and a partial enlarged sectional view showing the connection between a pressure sensor and the tank, respectively;

FIGS. 9a, 9b, 9c and 9d are a plan view, right side view, left side view and an enlarged longitudinal sectional view of a solenoid valve 42, respectively;

FIGS. 23a and 23b are flowcharts shematically showing operation of the processing unit CPU2 illustrated in FIG. 20.

DESCRIPTION OF PREFERRED EMBODIMENTS

Figure 1:
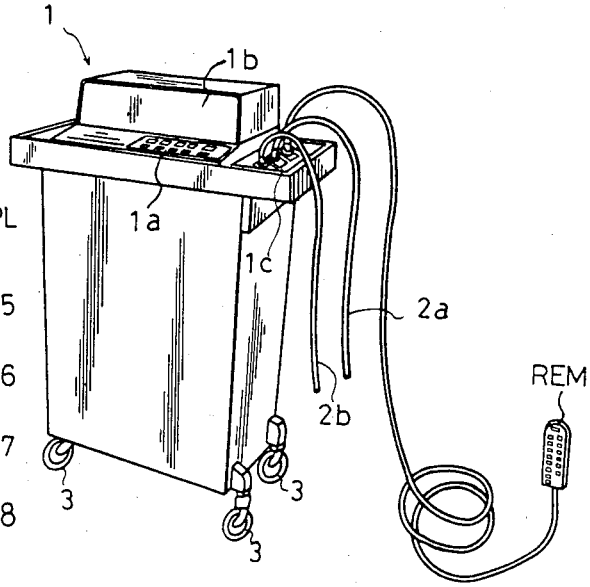
FIG. 1 is an external perspective view showing one embodiment of an artificial heart driving apparatus according to the invention.
Figure 2A:
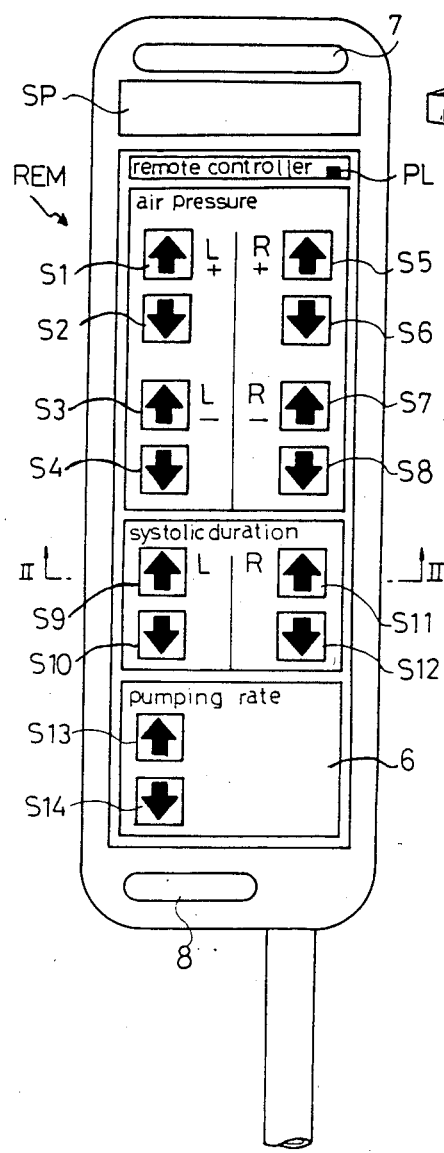
FIG. 2a is a front view of a remote control unit REM.
Figure 2B:
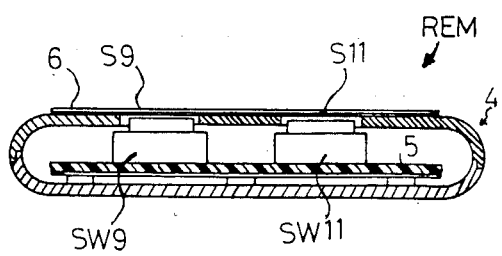

FIG. 1 shows an external apperance of an artificial heart driving apparatus of one type embodying the invention. Referring to FIG. 1, designated at 1 is a body of the artificial heart driving apparatus, 1a is a control panel, 1b is a display panel, and 1c is a connection panel. On a screen within the display panel 1b, there are indicated positive pressure, negative pressure and a duty ratio of positive and negative pressures for a right-hand heart, positive pressure, negative pressure and a duty ratio of positive and negative pressures for a left-hand heart, heart rate, and pressures (negative/positive) of the right- and left-hand systems. To the connection panel 1c are connected a cable for a remote control unit (or remote control means) which is detachable therefrom with a connector, and tubes 2a, 2b used for applying pressures to the right-hand and left-hand artificial hearts. The body 1 of the artificial heart driving apparatus is supported by four casters 3 in a movable manner. FIG. 2a is a front view of the remote control unit REM and FIG. 2b is an enlarged sectional view taken along the line II—II in FIG. 2a. Referring to FIGS. 2a and 2b, the remote control unit REM is able to remotely control all parameters of the artificial heart driving apparatus body and it includes fourteen control sections S1 to S14 in total. The control sections S1 to S4 function to instruct an increase in positive pressure, decrease in positive pressure, increase in negative pressure and a decrease in negative pressure for the left-hand artificial heart, respectively. The control sections S5 to S8 function to instruct an increase in positive pressure, decrease in positive pressure, increase in negative pressure and a decrease in negative pressure for the right-hand artificial heart, respectively. The control sections S9 and S10 function to instruct an increase and a decrease in duration of positive pressure or negative pressure (or duty ratio of positive and negative pressures) for the left-hand artificial heart, respectively, while the control sections S11 and S12 function to instruct an increase and a decrease in duration of positive pressure or negative pressure for the right-hand artificial heart, respectively. And the control sections S13 and S14 function to instruct as increase and a decrease in heart rate, respectively. Designated at PL is a light emitting diode which indicates that a power supply for the artificial heart driving apparatus comes on and that the REM is connected to the body, and SP is a speaker which generates a sound to inform that a switch is pressed down.

A casing 4 of the remote control board REM is formed of a synthetic resin. Within the casing 4 is fixed a printed circuit board 5 which mounts thereon key switches (e.g., SW9, SW11) at positions corresponding to the respective control sections, each key switch having a relatively short stroke. The casing 4 is formed with openings at positions also corresponding to the respective control sections and a flexible film 6 is coated to cover the surface of the casing 4 including those openings, so that the internal switches or so are waterproofed. The reference numerals 7 and 8 denote openings which are used for hanging the remote control board REM on any desirous position.

Figure 3:
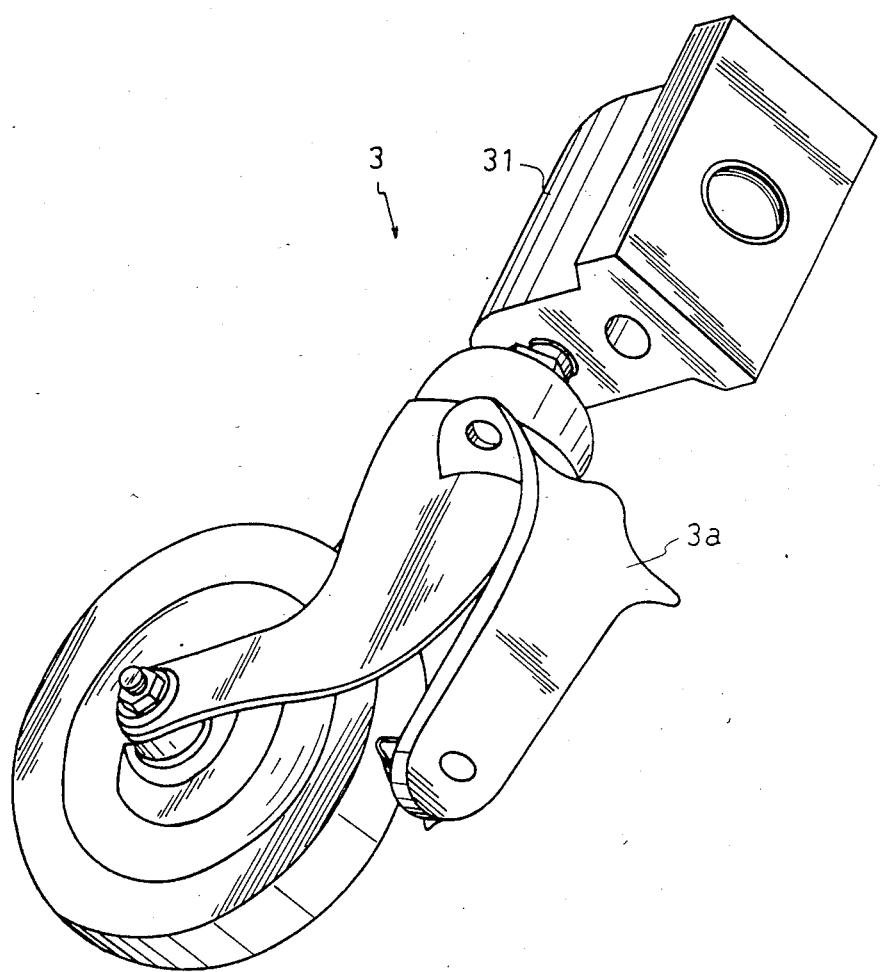
FIG. 3 is a perspective view of a caster.

FIG. 3 is a perspective view of a caster 3, FIGS. 4a, 4b, 4c and 4d are a front view, left side view, right side view and a vertical sectional view of a casing 31 which constitutes the caster 3, respectively, FIG. 5 is a front view of a bolt 32 used for fixing the caster, FIGS. 6a and 6b are a front view and a left side view of a stand 33 used for supporting the caster, respectively, and FIG. 7 is a partially broken front view showing the connection of the caster 3 and the body 1 of the artificial heart driving apparatus. The following description will be made by referring to FIG. 3, FIGS. 4a, 4b, 4c and 4d, FIG. 5, FIGS. 6a and 6b, and FIG. 7.

The casing 31 is formed with three holes 31a, 31b and 31c. One hole 31a serves to couple a caster body 3a with the casing 31, another hole 31b serves to receive a projection 34 of the stand 33, and still another hole 31c serves to receive the bolt 32. As shown in FIG. 5, the bolt 32 has a tapered head including serrations thereby to make it easy to grasp and hard to slip. The thread is formed only in a portion near the head. The stand 33 comprises a plate-like portion and the projection 34. The projection 34 includes a hole 34a which is communicated with the hole 31c in the casing 31 in the assembled state. The reference numeral 33a denotes holes each of which receives a bolt used for fixing the stand 33 to the body 1 of the artificial heart driving apparatus.

Normally, the caster 3 is integrally coupled to the body 1 of the artificial heart driving apparatus, as shown in FIG. 7. More specifically, the projection 34 of the stand 33 fixed to the body 1 of the artificial heart driving apparatus is inserted into the hole 31b of the caster 33, and then the hole 31c is aligned with the hole 34a. After that, the bolt 32 is inserted through thus aligned holes thereby to fix the caster 3 to the body 1. Designated at 35 is a sealing vinyl having been sterilized, and 36 is a packing.

The reason why the caster is fixed in a detachable manner in this way is in that the contaminated caster can be made exchangeable for the sterilized caster. When carrying the artificial heart driving apparatus into a clean room, an operating room or the like, the caster is exchanged from the artificial heart driving apparatus in the state as shown in FIG. 7 at an entrance of the clean room, etc. as follows. First, the bolt 32 is turned to be removed, and then the caster 3 is removed while turning it with respect to the projection 34, because the hole 31b and the projection 34 are in relatively firm engagement. After removing the packing 36 and the sealing vinyl 35, the sterilized caster is fitted over the projection 34 and then the sterilized bolt is inserted.

By so doing, it becomes possible to elminate a conventional need of sterilizing the caster which can not be covered with the sterilized sheet, when carrying the artificial heart driving apparatus from the normal room to the clean room or the like. And the invention just requires such simple work as exchanging the contaminated caster for new one prepared beforehand, so that the apparatus may be carried quickly.

Figure 8A:
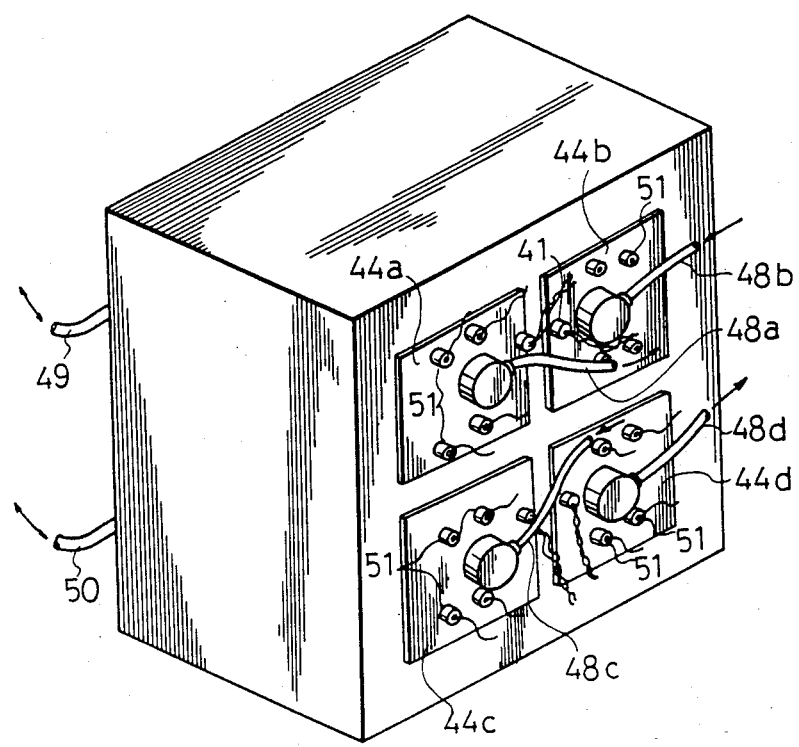

The following description will be made with reference to FIGS. 8a, 8b, 8c, 8d and 8e, which are a perspective view of a tank unit 40 installed within the body 1 of the artificial heart driving apparatus, a horizontal sectional view of the tank unit (or sectional view taken along the line VIIIb—VIIIb in FIG. 8c), a sectional view taken along the line VIIIc—VIIIc in FIG. 8b, a partial enlarged sectional view showing the connection between a terminal and a tank, and a partial enlarged sectional view showing the connection between a pressure sensor 41 and the tank, respectively.

The tank unit 40 includes four tanks (accumulators) and this one unit constitutes a part of both positive and negative pressure systems for a pair of (left and right) artificial hearts. Each of those four tanks includes two solenoid valves 42, 43 and a pressure sensor 41. The solenoid valve 43 is of a normal opening and closing control type, while the solenoid valve 42 is of a solenoid control valve whose opening degree is controlled in accordance with a level of energization as described later. The solenoid valve 42 within each block (or tank) of the positive pressure side has port 42a which is fixedly inserted into a hole 45b, or 45c formed in a panel 44b or 44c, while the other port is opened to a space within the block. The solenoid valve 42 within each block of the negative pressure side has one port 42b fixedly inserted into a hole 45a or 45d formed in a panel 44a or 44d, and the other port is opened to a space within the block. The solenoid valve 43 within each block has one port 43a which is opened to a space within the block, and the other port 43b which is fixedly inserted into a hole 46a, 46b in a panel 46 or a hole 47a, 47b in a panel 47.

Tubes 48a, 48b, 48c and 48d are respectively connected to the panels 44a, 44b, 44c and 44d so as to make communication with the holes 45a, 45b, 45c and 45d therein. The tubes 48a and 48d are connected to vacuum pumps serving as negative (or minus) pressure sources, while the tubes 48b and 48c are connected to compressors serving as positive (or plus) pressure sources. Both holes 46a and 46b in the panel 46 are communicated with each other and a tube 49 is connected to the common path. Likewise, both holes 47a and 47b in the panel 47 are communicated with each other and a tube 50 is connected to the common path. The tubes 49 and 50 are connected to the left- and right-hand artificial hearts, respectively.

Figures 8D, 8E:
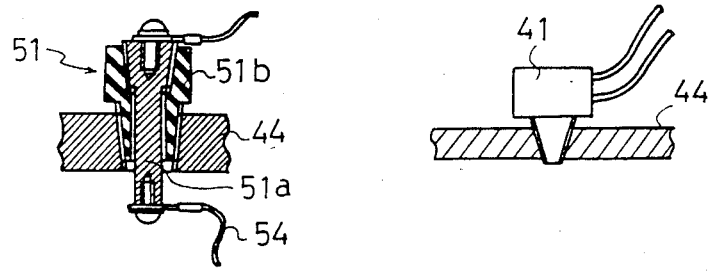
Figure 9B:
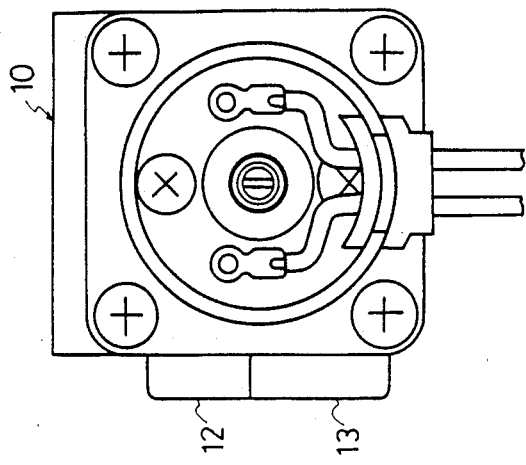
Figure 9A:
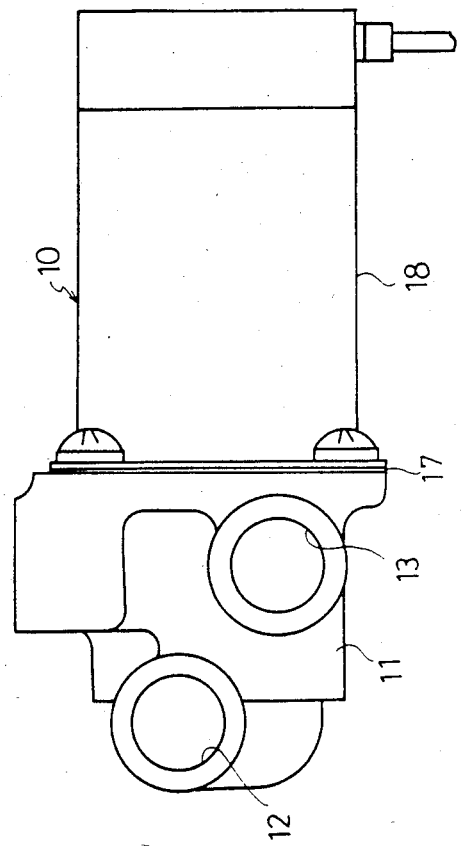

Each of the panels 44a, 44b, 44c and 44d includes four terminals 51 and a pressure sensor 41 which are fixed thereto. The terminals 51 and the pressure sensor 41 are mounted in such a manner as shown in FIGS. 8d and 8e. Each terminal 51 comprises a bar-like conductor 51a and an insulative nipple 51b for holding the conductor 51a. The insulative nipple 51b is formed of Teflon. The panel 44 is formed with tapered openings each having the thread on its inner surface, and the insulative nipple 51b has a shape corresponding to the tapered opening. The conductor 51a and the insulative nipple 51b are fixed to each other similarly through tapered threads. These tapered threads also serve as a sealing member, so that a need of providing a special sealing member is eliminated. Lead wires 54 from solenoids of the solenoid valves 42 and 43 are connected to the respective terminals 51 through connectors 52 and 53. The pressure sensor 41 is fixed to the panel 44 through the tapered threads similarly to the terminals 51.

The following description will be made by referring to FIGS. 9a, 9b, 9c and 9d, which are a plan view, right side view, left side view and an enlarged longitudinal sectional view of the solenoid valve (or solenoid control valve) 42 used in this embodiment respectively. A valve housing 11 of the solenoid control valve 42 is formed with a first port 12 and a second port 13. A space within the housing 11 is divided by a valve seat 14 into a first inner chamber 15 in communication with the first port 12 and a second inner chamber 16 in communication with the second port 13. A coil case 18 formed of magnetic substance is fixed to the valve housing 11 through a sealing material 17. A coil bobbin 20 including a coil 19 wound therearound is fitted in the case 18 and it is supported by base 21 and 22 formed of magnetic substance. A fixed magnetic substance core 23 is fixed to the base 21. The core 23 is hollow and a guide rod 24 formed of non-magnetic substance is extended to pass therethrough. A movable magnetic substance core 25 is fixed to the guide rod 24. The guide rod 24 is biased leftward by a coil spring 26 which is in contact with one end of the rod. The other end of the guide rod 24 extends through a bearing 27 and bellows 28 and has a valve body 29 fixed at its tip end. A space within the bellows 28 is communicated through small ports 30 and 37 with the first inner chamber 15 (in the illustrated state) or the second inner chamber 16 (when the guide rod 24 is driven rightward).

When the coiled 19 is energized, there occurs magnetic flux which circulates through the core 23 - core 25 - base 22 - case 18 - base 21 - core 23. This generates a force acting upon the core 25 to attract the same toward the core 23, whereby the rod 24 moves rightward until the attracting force will become equal to a repellent force of the coil spring 26 and hence the valve body 29 is departed from the valve seat 14 by a distance corresponding to a degree of the attracting force. An end face 23a of the core 23 is shaped into the form of a letter E, while an end face 25a of the core 25 has a recessed shape to receive a central projected portion of the end face 23a. The inner surfaces 23b between both end projected portions and the central projected portion of the E-shaped end face 23a are tapered as seen from FIG. 9d. The presence of these tapered surfaces ensures that a ratio of energization level of the coil and shift amount of the rod 24 (or a gap between both faces 23a and 25a) is held in a proportional relationship in a wide range. Moreover, the solenoid valve of this kind has good responsivity in its movable portions and permits opening and closing control at a high speed.

Figure 10:
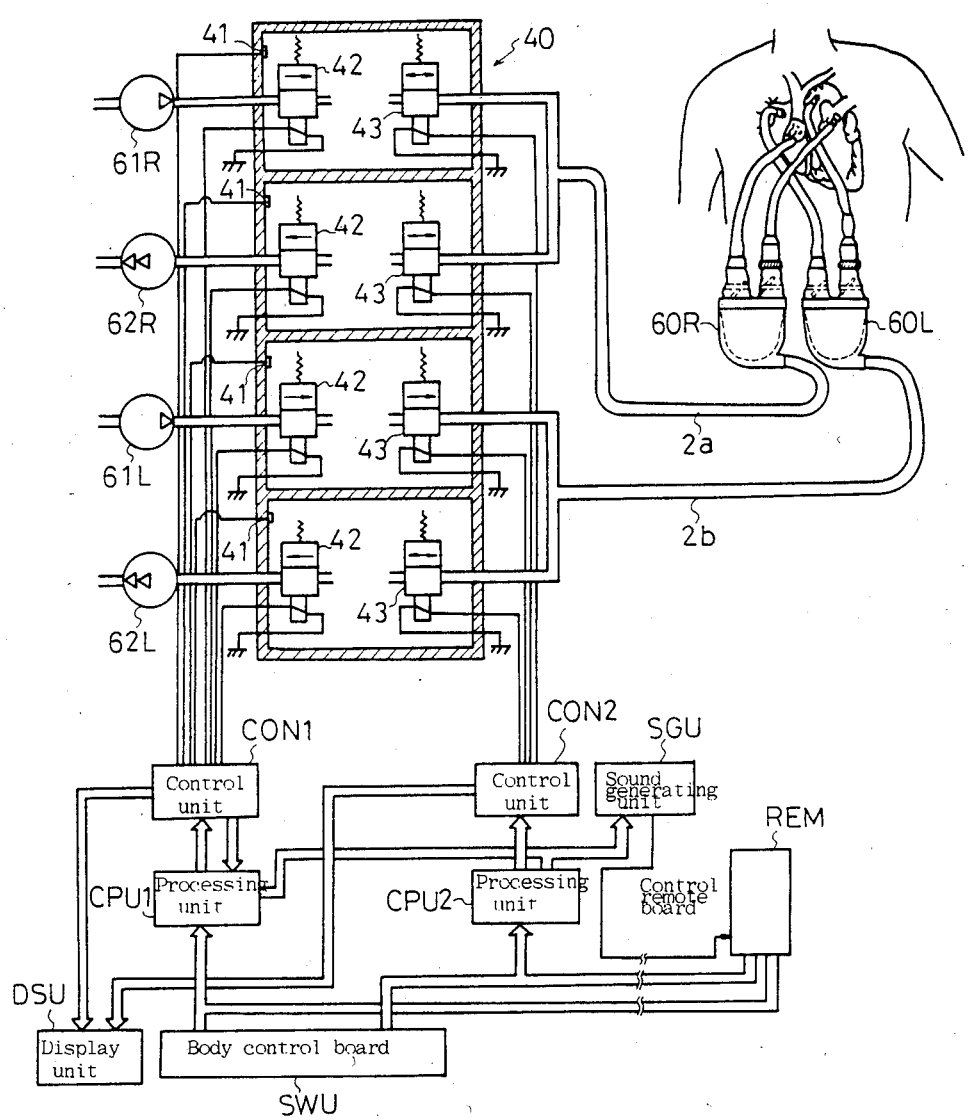
FIG. 10 is a block diagram schematically showing the artificial heart driving apparatus illustrated in FIG. 1.

FIG. 10 illustrates schematically the artificial heart driving apparatus shown in FIG. 1 together with the artificial hearts. Referring to FIG. 10, designated at 60R and 60L are artificial hearts which are connected to the artificial heart driving apparatus through the tubes 2a and 2b, respectively. These tubes 2a and 2b are connected to the corresponding output terminals of the tank unit 40. Designated at 61R and 61L are compressors, while 62R and 62L are vacuum pumps. Solenoids of four solenoid valves 42 and the pressure sensors 41 are connected to a control unit CON1, and four solenoid valves 43 are connected to a control unit CON2.

These solenoid valves 42 and 43 in total number eight are constructed as shown in FIGS. 9a, 9b, 9c and 9d. Besides, since air flows from the input port to the output port in the positive pressure system and it flows from the output port to the input port in the negative pressure system, the input and output ports of the solenoid valves are connected in a reversed relationship in the positive and negative pressure systems.

Processing units CPU1 and CPU2 are respectively connected to the control units CON1 and CON2. Control terminals for instructing changes in positive pressure, negative pressure, heart rate and duty ratio are connected to input ports of the processing units CPU1 and CPU2. The control terminals comprise a body control board SWU provided on the control panel 1a of the artificial heart driving apparatus body 1 and a remote control board REM used in remote control. The body control board SWU and the remote control board REM are connected in parallel as described later. A predetermined signal from a sound generating unit SGU is supplied to the remote control board REM. The sound generating unit SGU is controlled by the processing units CPU1 and CPU2. The display unit DSU comprises a 7-segment, light emitting diode (LED) type indicator or so used for displaying numerals, and it is driven by a digit driving signal and a segment driving signal from both the control units CON1 and CON2 in a dynamic manner.

Figure 11:
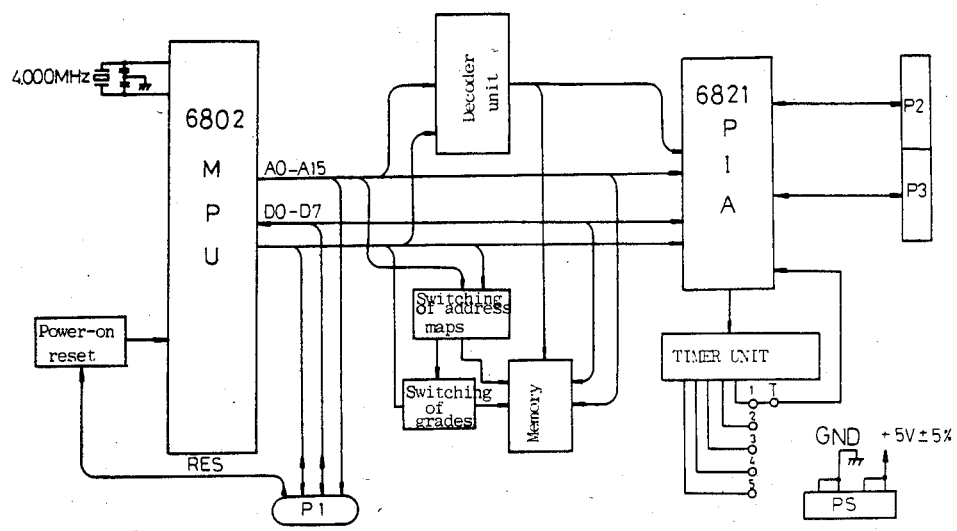
FIG. 11 is a block diagram showing processing units CPU 1 and 2 illustrated in FIG. 10.

FIG. 11 illustrates a constitution of the processing unit CPU1 shown in FIG. 10. The control units CPU1 and CPU2 have the identical construction. As this processing unit (or microcomputer) is used a single board microcomputer unit H62SCO1 manufactured by Hitachi Ltd. H62SCO1 employs a microcomputer of 6802 series and includes I/O ports, timer, RAM, ROM, etc. In this embodiment, HM6116 of CMOS type is used as RAM.

Figure 12:
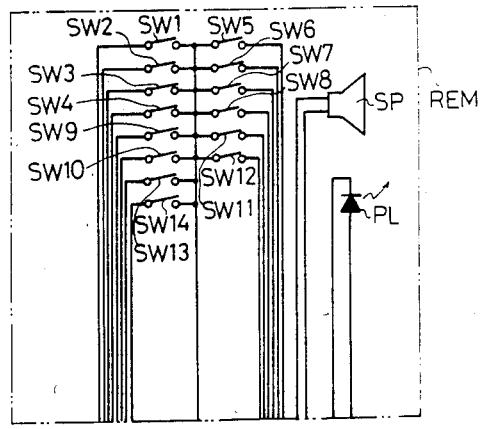
FIG. 12 is a circuit diagram showing a circuitry of the remote control unit.

FIG. 12 shows a circuitry of the remote control unit REM. In this figure, desgniated at SW1 to SW14 are key switches which are provided corresponding to the control sections S1 to S14 shown in FIG. 2a, SP is a speaker and PL is a light emitting diode.

Figure 13A:
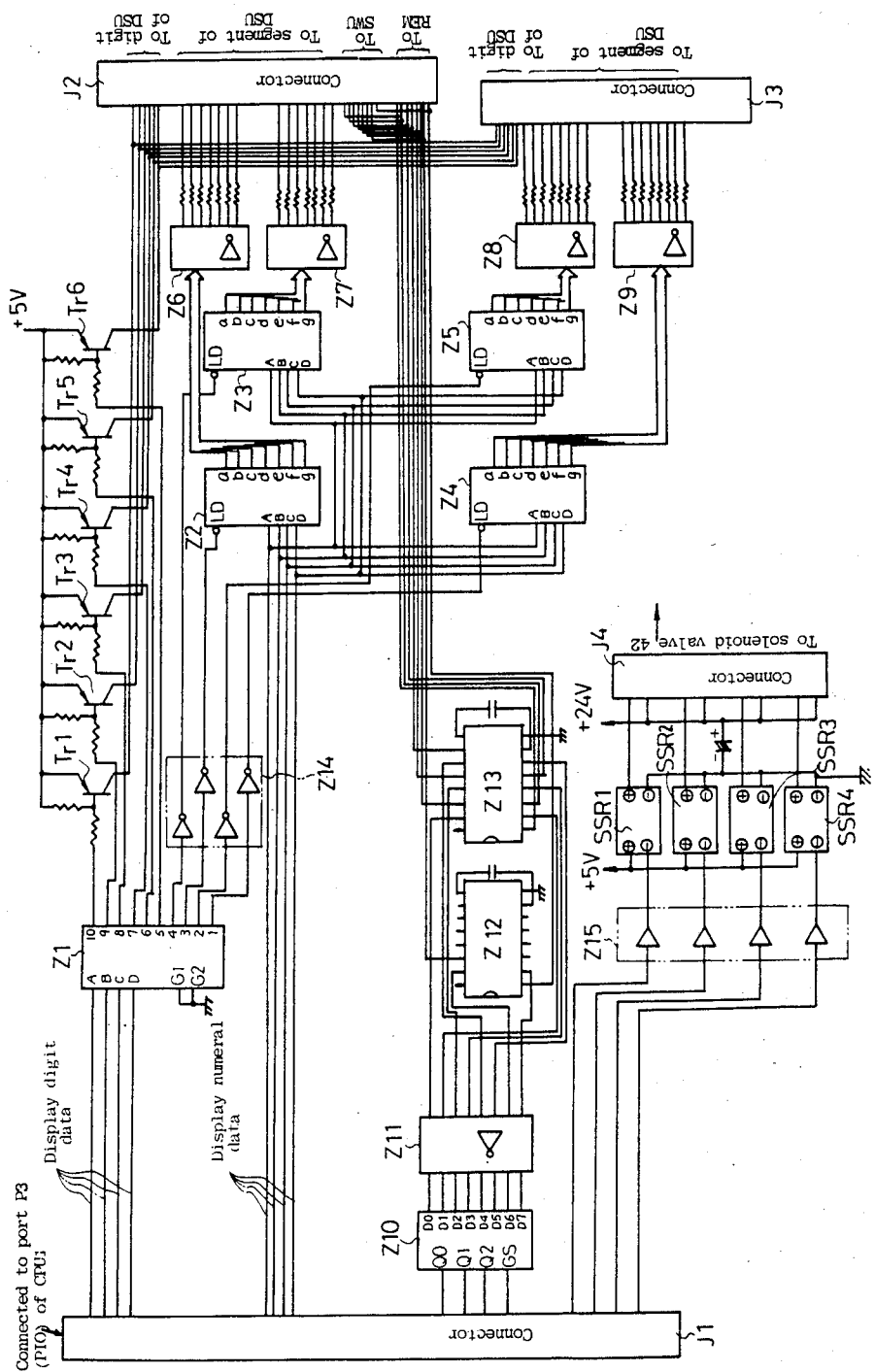
FIGS. 13a and 13b are circuit diagrams showing a circuitry of the control unit CON 1 illustrated in FIG. 10.
Figure 13B:
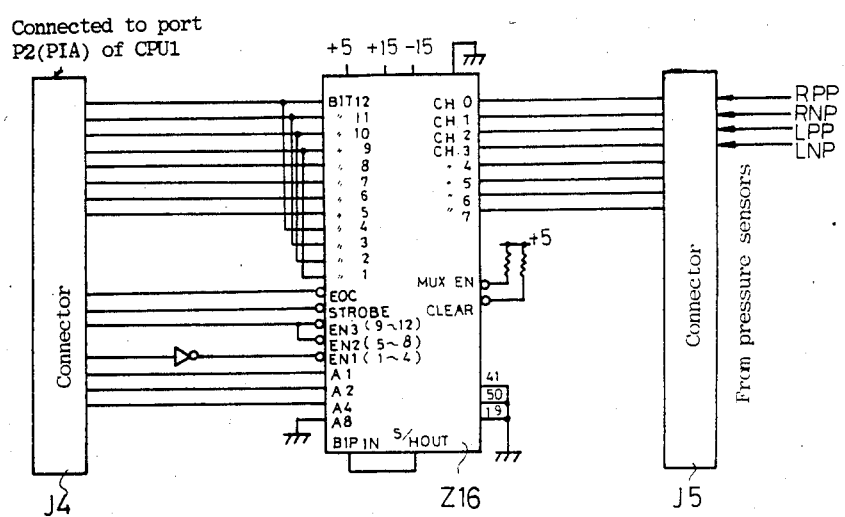

FIGS. 13a and 13b illustrate a circuitry contained in the control unit CON1. A list of integrated circuits (IC's) used in the control unit CON1 is given in the following Table 1.

TABLE 1

| No. | Item | Maker | Function |
| --- | --- | --- | --- |
| Z1 | SN75154 | T.I | 4–16 decoder |
| Z3~Z5 | MC14543 | Motorola | BCD-7 seg decoder |
| Z6~Z9 | ULN2003 | T.I | Driver |
| Z10 | MC14537 | Motorola | Priority encoder |
| Z11 | MC14069 | Motorola | Inverter |
| Z12,Z13 | MC14490 | Motorola | Chattering removal |
| Z14 | SN7404 | T.I | Inverter |
| Z15 | SN7407 | T.I | Buffer (OC) |
| Z16 | HDAS-16 | DATEL | A/D converter |

The following description will be made first by referring to FIG. 13a. A connector J1 is connected to an output port P3 of the processing unit CPU1, and for the purpose of displaying in a dynamic driving manner, display data fed from the CPU1 is divided into two BCD signals representing display digit data and display numeral data. The display data output from the CPU1 includes information of positive pressure and negative pressure in both left- and right-hand systems. An integrated circuit Z1 decodes the BCD signal representing the display digit data and then apply thus decoded signals to transistors Tr1 to Tr6 and inverters Z14. The transistors Tr1 to Tr6 are connected to anodes (or digit electrodes) of the light emitting diode type indicator. Integrated circuits Z2 to Z5 serve to convert the BCD signal representing the display numeral data into 7-segment signals, which are applied through drivers Z6 to Z9 to respective cathodes (or segment electrodes) of the light emitting diode type indicator. Key switch contacts of the body control board SWU and key switch contacts of the remote control board REM are connected in parallel in the vicinity of a connector J2, and then they are connected to integrated circuits Z12 and Z13. These integrated circuits Z12 and Z13 include therein a circuit for removing chattering due to the mechanical contacts, thereby to apply signals deprived of such chattering to an integrated circuit Z10 through inverters Z11. The integrated circuit Z10 outputs binary codes in accordance with the key switches pressed down to the microcomputer CPU1 with the preset priority. Designated at SSR1 to SSR4 are solid state relays which are controlled to be on and off with the output port of the microcomputer CPU1 through buffers Z15. Output terminals of the solid state relays SSR1 to SSR4 are connected to the corresponding solenoid valves 42 through a connector J4, respectively.

Referring now to FIG. 13b designated at Z16 is a 16-channel, 12-bit A/D converter HDAS-16MC manufactured by DATEL Ltd. Terminals BIT1 to BIT12 of Z16 serve as signal output terminals, and the terminals BIT1 to BIT4 and the terminals BIT9 to BIT12 are connected to each other. The input port of the microcomputer CPU1 receives a 12-bit signal which is applied thereto in twice by 8 bits at a time. Switching between the terminals BIT1 to 4 and the terminals BIT5 to 12 is effected in such a manner that the CPU1 controls respective terminals EN1, EN2 and EN3 of the converter Z16. Terminals A1, A2, A4 and A8 are used to select input channels. Although the HDAS-16 has an input port comprising 16 channels, in this embodiment 8 channels among them are connected to a connector J5 and 4 channels among those 8 channels receive signals from the respective pressure sensors 41, that is, a right positive pressure signal RPP, right negative pressure signal RNP, left positive pressure signal LPP and a left negative pressure signal LNP.

Figure 15:
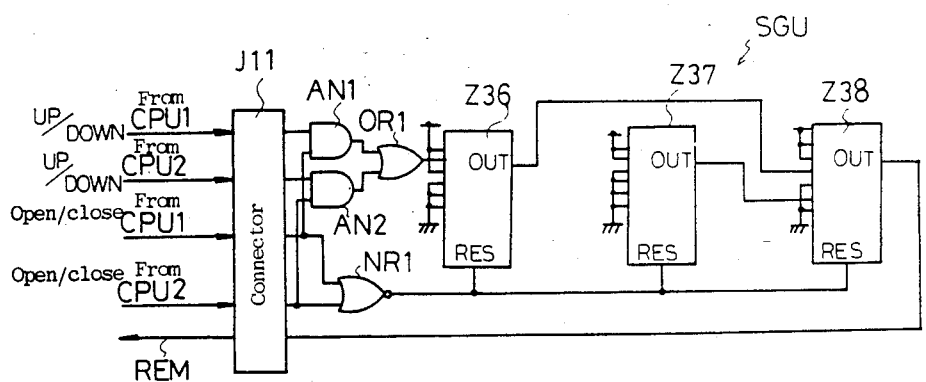
FIG. 15 is a block diagram showing a circuitry of a sound generating unit SGU.
Figure 14:
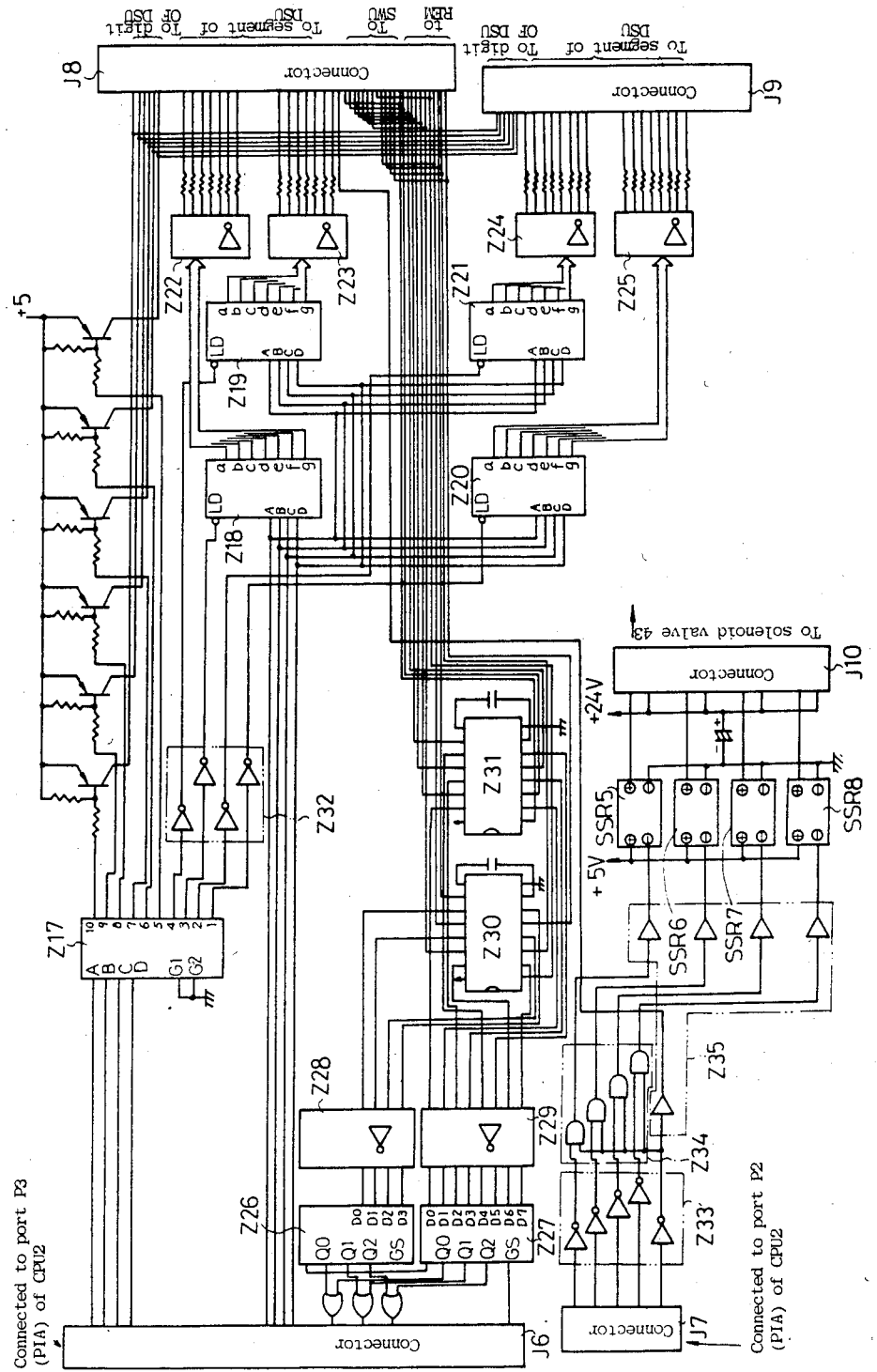
FIG. 14 is a circuit diagram showing a circuitry of the control unit CON 2 illustrated in FIG. 10.

FIG. 14 is a circuit diagram showing a circuitry of the control unit CON2, and FIG. 15 is a block diagram showing a circuitry of the sound generating unit SGU. The following description will be made by referring to FIGS. 14 and 15. A list of integraged circuits used in the control unit CON2 and the sound generating unit SGU is given in the following Table 2.

TABLE 2

| No. | Item | Function |
| --- | --- | --- |
| Z17 | SN75154 | 4-16 decoder |
| Z18~Z21 | MC14543 | BCD - 7 seg decoder |
| Z22~Z25 | ULN2003 | Driver |
| Z25,Z27 | MC14537 | Priority encoder |
| Z28,Z29 | MC14069 | Inverter |
| Z30,Z31 | MC14490 | Chattering removal |
| Z32,Z33 | SN7404 | Inverter |
| Z34 | SN7408 | AND gate |
| Z35 | SN7407 | Buffer (OC) |
| Z36 Z38 | 8640 | Oscillator |

The control unit CON2 has a similar structure to that of the aforesaid control unit CON1, but an A/D converter is not included in the control unit CON2 because it has no function to detect pressures. Connectors J6 and J7 are connected to ports P3 and P2 of the processing unit CPU2, respectively. A connector J10 is connected to solenoids of the respective solenoid valves 43. To integrated circuits Z30 and Z31 are connected through a connector J8 key switch contacts of the body control board SWU and the remote control board REM, which contacts serve to instruct an increase and a decrease in heart rate, and an increase and a decrease in a ratio of positive pressure applying period and negative pressure applying period for the left and right artificial hearts, respectively. The sound generating unit SGU includes three integrated circuits Z36 to Z38 as main parts. Each of these integrated circuits Z36 to Z38 issues from its output terminal OUT a signal having the frequency in accordance with the state of six input ports thereof.

A connector J11 receives from both CPU1 and CPU2 "ON/OFF" signals which indicate whether the keys are pressed down or not, and also "UP/DOWN" signals which indicate that which one of an increase and a decrease is instructed by the pressed keys. These signals being applied from the CPU1 and CPU2. With the keys not being pressed down, reset input terminals RES of the integrated circuits Z36 to Z38 assume a high level H so as to reset Z36 to Z38. In the state that the reset input terminals RES assume a low level L, the integrated circuit Z36 issues from its output terminal a pulse signal of 3.2 KHz or 1.6 KHz in accordance with a logical level at the output terminal of an OR gate OR1. The integrated circuit Z37 outputs a pulse signal of 2 Hz at all times with its RES terminal assuming a low level L and then applies this output pulse signal to an input port of Z38. The integrated circuit Z38 issues at its output terminal directly the pulse signal of 3.2 KHz or 1.6 KHz applied from Z36 with the output terminal of Z37 assuming a high level H, while Z38 issues at its output terminal a signal with half the frequency of the pulse signal applied from Z36 with the output terminal of Z37 assuming a low level L.

Therefore, when the left-hand pressure increasing control section S1 on the remote control board REM is pressed down, for example, the UP/DOWN signal from the CPU1 assumes H and the OFF/ON signal from the CPU1 assumes H, so that a pulse signal of 3.2 KHz appears at the output terminal of Z36 and a pulse signal changing in the frequency from 3.2 Khz to 1.6 KHz or vice versa with intervals of 0.5 second appears at the output terminal of Z38. Alternatively, when the left-hand pressure decreasing control section S2 is pressed down, a pulse signal of 1.6 KHz appears at the output terminal of Z36 and a pulse signal changing in the frequency from 1.6 KHz to 0.8 KHz or vice versa with intervals of 0.5 second appears at the output terminal of Z38. These signals are applied to the speaker on the remote control board REM.

Figure 16C:
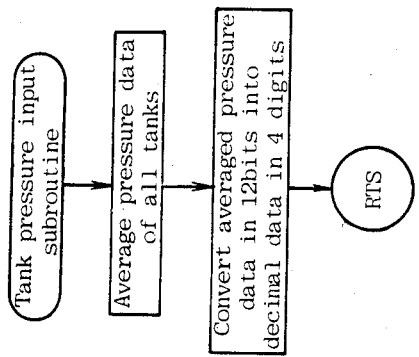
FIGS. 16a, 16b and 16c are flowcharts of a main routine, an interrupt processing routine and a subroutine showing an operation flow of the processing unit CPU1, respectively.
Figure 16B:
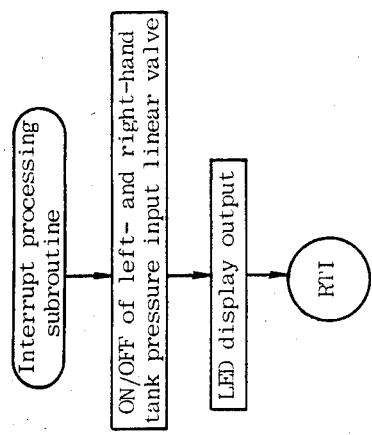
Figure 16A:
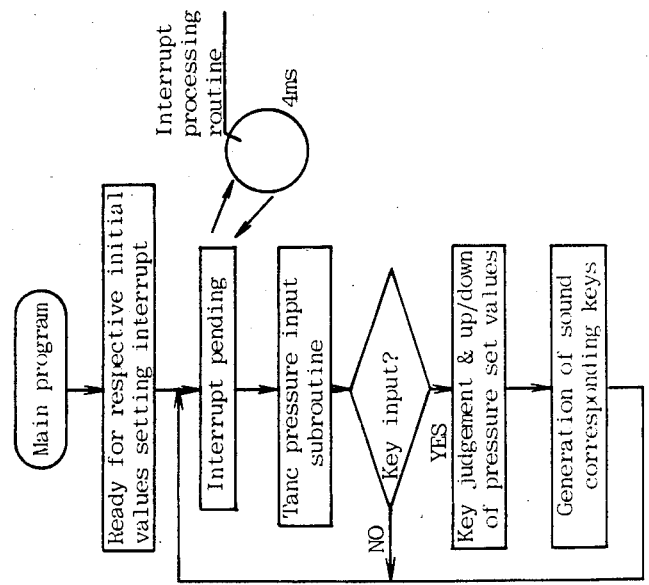

An operation flow of the processing unit CPU1 is schmatically illustrated in FIGS. 16a, 16b and 16c, which show flows of a main program, an interrupt processing program and a tank pressure input subroutine, respectively. Operation of the CPU1 will be now described by referring to FIGS. 10, 13a, 13b, 16a, 16b and 16c. In brief, the processing unit CPU1 performs reading of key inputs from the body control board SWU or the remote control board REM, reading of respective tank pressures (i.e., outputs of the pressure sensors 41), constant tank pressure control of the respective pressures (i.e., duty control for the solenoid valves 42), changes in the pressure parameters in accordance with key inputs, output of display data, and instruction of generating a sound.

When the power supply comes on, the respective parameters are made to have initial values thereby to set the interrupt enable state. In this embodiment, initial values of RPP, RNP, LPP and LNP are set at +30, −30, +100 and −50 (mmHg), respectively, and upper/lower limits of those pressures are set at +150/0, 0/−100, +300/0 and 0/−150 (mmHg), respectively. Interruption is periodically generated with intervals of 4 ms using a timer within the CPU1. When the interruption occurs, the microprocessor executes the interrupt processing routine as shown in FIG. 16b. In the interrupt processing routine, the A/D converter Z16 is first selected and its input channel is switched in the sequence of CH0, CH1, CH3 and CH4, thereby to perform A/D conversion of the respective tank pressure RPP, RNP, LPP and LNP in turn and then read thus converted digital data.

Moreover, "1" or "0" is output to the predetermined ports of P3 to control the solid state relays SSR1 to SSR4, so that four solenoid valves 42 are turned on or off. This on/off switching is carried out in accordance with the duty parameter preset in a memory of the CPU1 in such a manner that the solenoid valves are turned from the on-state to the off-state every n1 times interruptions and are turned from the off-state to the on-state every n2 times interruptions. Thus, a duty ratio of on-state time and off-state time for each solenoid valve 42 is varied along with changes in a value of the parameter. The tank pressure can be held at a predetermined level by controlling such duty ratio in accordance with the result of comparison between the detected pressure and the target pressure for the tank. In the tank pressure input subroutine, pressure data of the respective tanks read from the A/D converter Z16 are averaged, and then the data thus averaged are converted into 4-digit decimal data for display. The reason why the pressure data are averaged is in eliminating minute fluctuations in pressure for a short period of time which are caused upon opening and closing of the valves. When there occurs a key input, it is judged that which key was pressed down and then a value of the parameter corresponding the pressed key is increase (or decreased) gradually. At the same time, it is also judged that which one of an increase and a decrease is indicated by the pressed key, and then both OFF/ON signal and UP/DOWN signal are applied to the connector J11, so that a given sound is generated from the speaker on the remote control board REM. Besides, a mnemonic code RTI shown in FIG. 16b represents a return instruction (i.e., return from interrupt), while a mnemonic code RTS shown in FIG. 16c represents a return instruction (i.e., return from subroutine).

Figure 17:
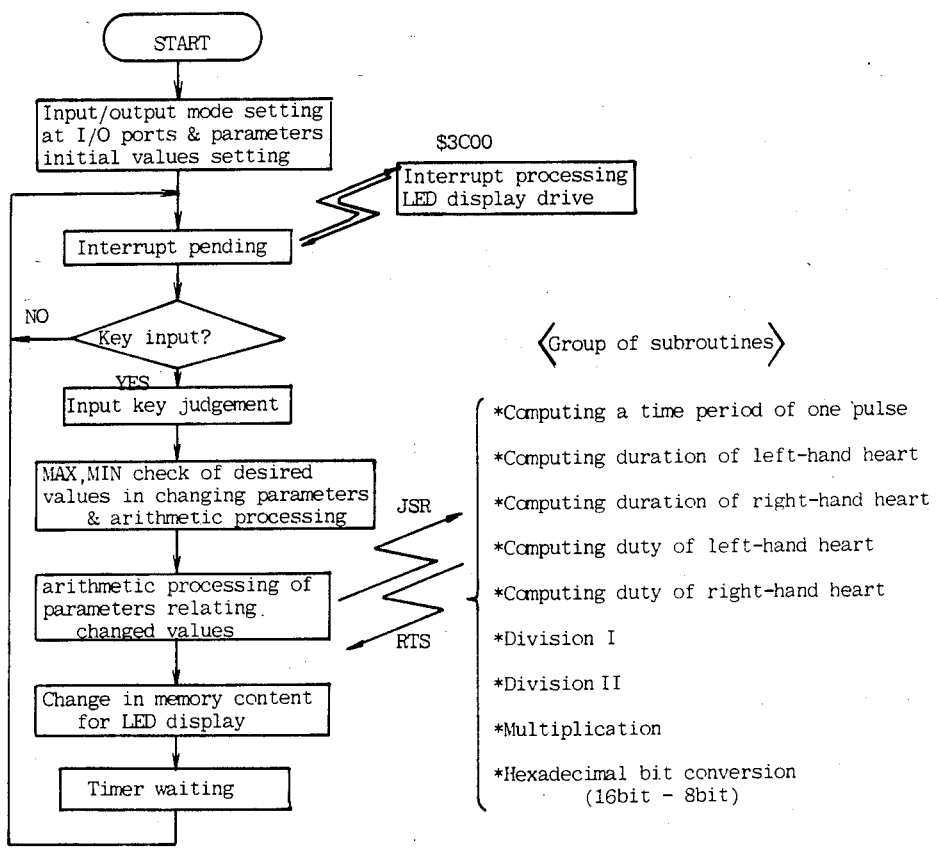
FIG. 17 is a flowchart schematically showing operation of the processing unit CPU2.

FIG. 17 shows a schematic operation flow of the processing unit CPU2. Operation of the processing unit CPU2 will be now described with reference to FIG. 17. When the power supply comes on, the microprocessor sets first the respective I/O ports at the initial state so that the parameters such as heart rate and a ratio of positive pressure applying time and negative pressure applying time (that is, duty ratio or duration of positive/negative pressure) for the left- and right-hand artificial hearts are made to have their initial values. In this embodiment, the initial values of the respective parameters are set such that heart rate is 100 rpm, a duty ratio of the left-hand artificial heart is 45% (or duration of 270 ms), and a duty ratio of the right-hand artificial heart is 55% (or duration of 330 ms). In the interrupt processing, a logical level at the predetermined output ports is updated from "1" to "0" or vice versa at certain timing in accordance with the given parameter (i.e., heart rate), thereby to control the solid state relays SSR5 to SSR8 and then open or close the solenoid; alve 43. At the same time, output of the display data (comprising digit data and segment data) is effected. When there occurs a key input, it is judged that which key was pressed down, and a value of the parameter corresponding to the pressed key is incremented or decremented during press operation of the key while confirming that its value will not exceed the upper or lower limit. Various parameters relating to that parameter are also subjected to arithmetic processing. This processing is carried out after jumping to the respective subroutines. A group of subroutines comprises a subroutine for computing a time period of one pulse in terms of heart rate, a subroutine for computing duration of the left-hand artificial heart, a subroutine for computing duration of the right-hand artificial heart, a subroutine for computing a duty ratio of the left-hand artificial heart, a subroutine for computing a duty ratio of the right-hand artificial heart, a subroutine for doing division, a subroutine for doing multiplication and so on. After completion of these calculations, the updated values of the respective parameters are stored in a memory for display and then the flow returns to interrupt standby processing after a predetermined period of time has lapsed. Upon subsequent interruption, the updated data are displayed.

Figure 18:
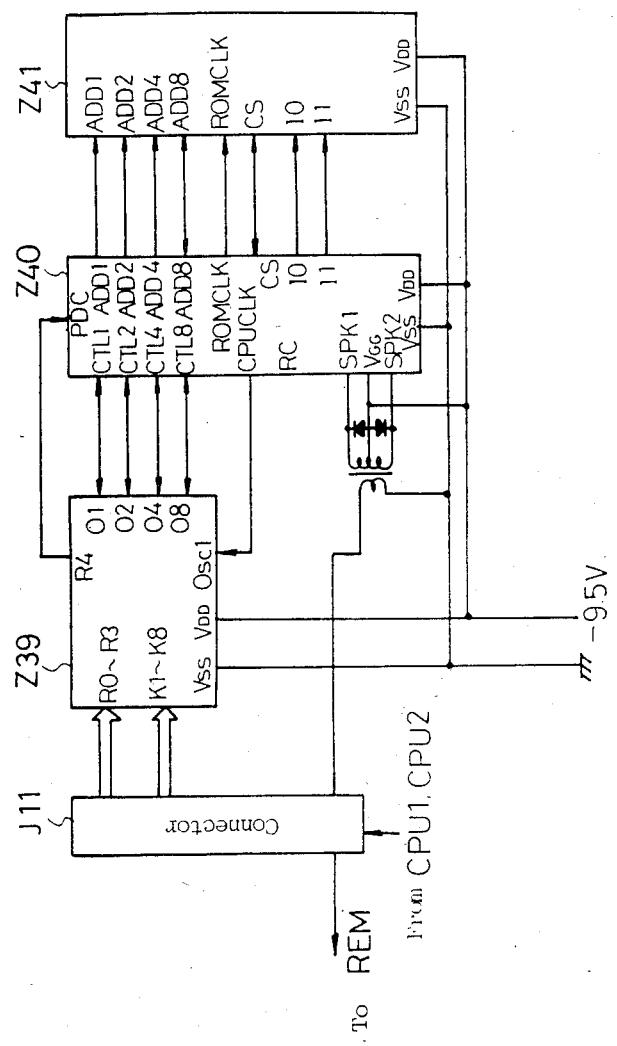
FIG. 18 is a block diagram of a sound generating unit according to a modified embodiment of the invention.

In the above-mentioned embodiment, a duty ratio of opening time and closing time is changed by energizing the solenoid valves 42 to be opened and closed at all times thereby to control pressures, but the solenoid valve 42 may be energized only when an output signal from the corresponding pressure sensor 41 exceeds a predetermined value. Also in this embodiment, a sound with the given frequency is generated from the speaker on the remote control board REM, but a voice indicating the parameter in accordance with the pressed key may be output. In this case, it is enough to modify the sound generating unit into such a circuitry as shown in FIG. 18. Referring to FIG. 18, designated at Z39, Z40 and Z41 are respectively TMS1000, TSM5100 and TMS6100 manufactured by Texas Instrument Ltd. TMS1000 is of a microcomputer, TMS5100 is of a voice synthetic chip, and TMS6100 is of a mask ROM of 128 Kbit. The connector J11 is connected to the processing units CPU1 and CPU2 which output the predetermined voice generating instructions to the microprocessor Z36, and a voice signal output from Z37 is supplied to the speaker on the remote control board REM.

Another embodiment of the invention will be described hereinafter. In brief, this modified embodiment includes one backup driving system in addition to the pair of two artificial heart driving systems used in the embodiment as mentioned above. And as required, the driving system under operation can be switched to the backup driving system or vice versa in a safe manner. External appearance and casters of the apparatus are identical to those in the foregoing embodiment. Identical parts to those in the foregoing embodiment will be described under the identical symbols.

Figure 19A:
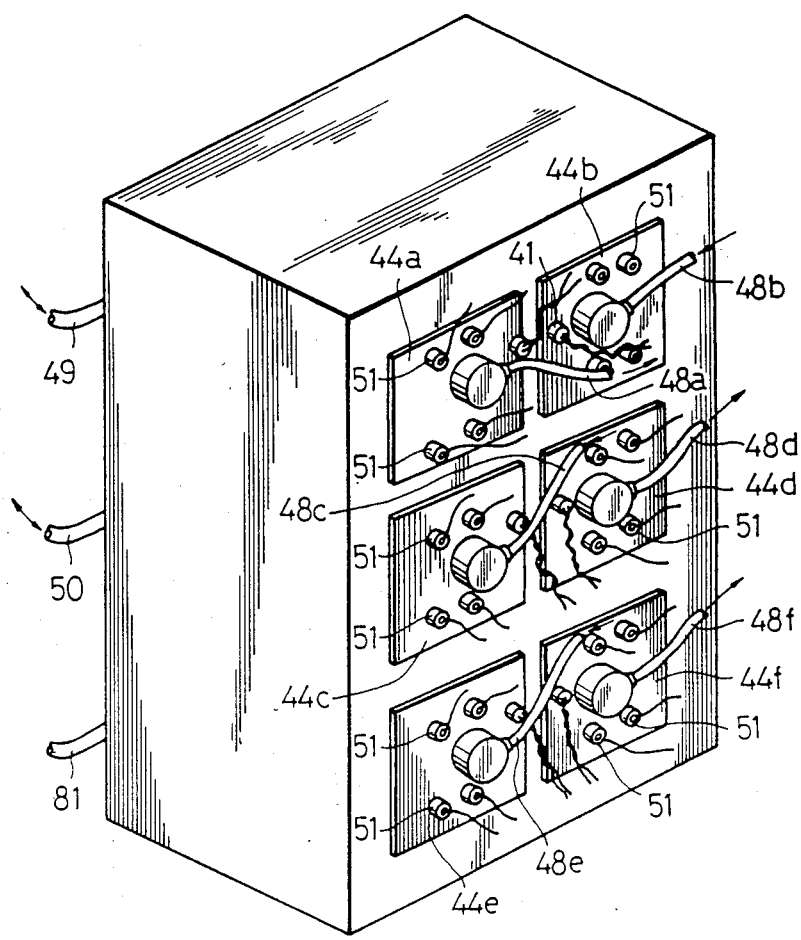
FIGS. 19a, 19b, 19c, 19d and 19e are a perspective view showing a tank unit within the artificial heart driving apparatus according to another embodiment of the invention, a horizontal sectional view of the tank unit, a sectional view taken along the line X IXc—X IXc in FIG. 19b, a partial enlarged sectional view showing the connection between a terminal and a tank, and a partial enlarged sectional view showing the connection between a pressure sensor and the tank, respectively.
Figure 19D:
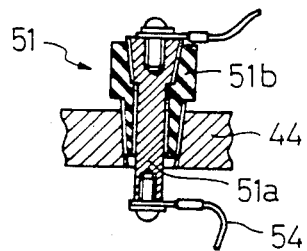
Figure 19E:
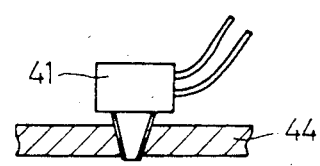
Figure 19C:
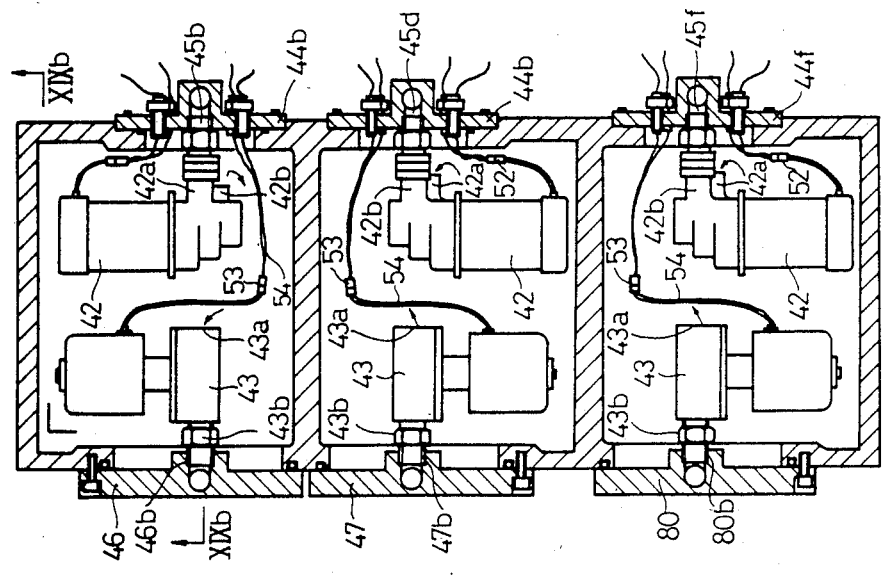
Figure 19B:
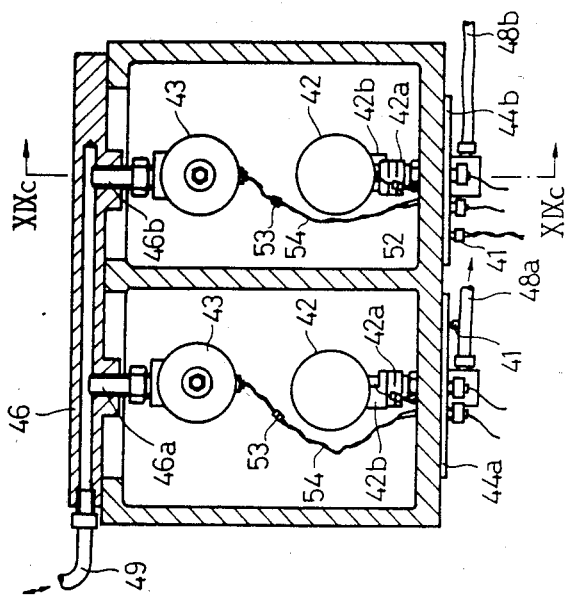

The following description will be made with reference to FIGS. 19a, 19b, 19c, 19d and 19e, which are a perspective view of a tank unit 40 provided within the body 1 of the artificial heart driving apparatus, a horizontal sectional view (i.e., sectional view taken along the line X IXb—X IXbin FIG. 19c), a sectional view taken along the line X IXc—X IXc in FIG. 19b, a partial enlarged sectional view showing the connection between a terminal and a tank, and a partial enlarged sectional view showing the connection between a pressure sensor 41 and the tank, respectively. The tank unit 40 includes six tanks (accumulators) and this one unit constitutes a part of both positive and negative pressure systems for a pair of (left and right) artificial hearts as well as backup positive and negative pressure systems.

Each of those six tanks includes two solenoid valves 42, 43 and the pressure sensor 41. The solenoid valves 42 and 43 are the same type as those used in the foregoing embodiment. The solenoid valve 42 within each block (or tank) has an input port 42a and an output port 42b either of which is fixedly inserted into a hole 45a, 45b, 45c or 45d formed in a panel 44a, 44b, 44c or 44d, while the other port (i.e., the remaining output port or input port) is opened to a space within the block. The solenoid valve 43 within each block has one port 43a which is opened to a space within the block, and the other port 43b is fixedly inserted into a hole 46a, 46b in a panel 46, a hole 47a, 47b in a panel 47, or a hole 80a, 80b in a panel 80. Tubes 48a, 48b, 48c, 48d, 48e and 48f are respectively connected to the panels 44a, 44b, 44c, 44d, 44e and 44f so as to make communication with the holes 45a, 45b, 45c, 45d, 45e and 45f therein. The tubes 48a, 48d and 48f are connected to a vacuum pump serving as a negative pressure source, while the tubes 48b, 48c and 48e are connected to a compressor serving as a positive pressure source. Both holes 46a and 46b in the panel 46 are communicated with each other and a tube 49 is connected to the common path. Likewise, both holes 47a and 47b in the panel 47 are communicated with each other and a tube 50 is connected to the common path. Also, both holes 80a and 80b in the panel 80 are communicated with each other and a tube 81 is connected to the common path. The tubes 49 and 50 are connected to the left- and right-hand artificial hearts, respectively, while the tube 81 is connected to two solenoid valves 71R and 71L (shown not in FIGS. 19a to 19e but in FIG. 20) at one side thereof. The solenoid valves 71R and 71L in turn are connected to the right- and left-hand artificial heart at the other side thereof.

Each of the panels 44a, 44b, 44c, 44d, 44e and 44f includes four terminals 51 and the pressure sensor 41 which are fixed thereto. The terminals 51 and the pressure sensor 41 are mounted in such a manner as shown in FIGS. 19d and 19e. Each terminal 51 comprises a bar-like conductor 51a and an insulative nipple 51b for holding the conductor 51a. The insulative nipple 51b is formed of Teflon. The panel 44 is formed with tapered openings each having the thread on its inner surface, and the insulative nipple 51b has a shape corresponding to the tapered opening. The conductor 51a and the insulative nipple 51b are fixed to each other similarly through tapered threads. These tapered threads serve as also a sealing, so that a need of providing a special sealing member is eliminated. Lead wires 54 from solenoids of the solenoid valves 42 and 43 are connected to the respective terminals 51 through connectors 52 and 53. The pressure sensor 41 is fixed to the panel 44 through the tapered threads similarly to the terminals.

Figure 20:
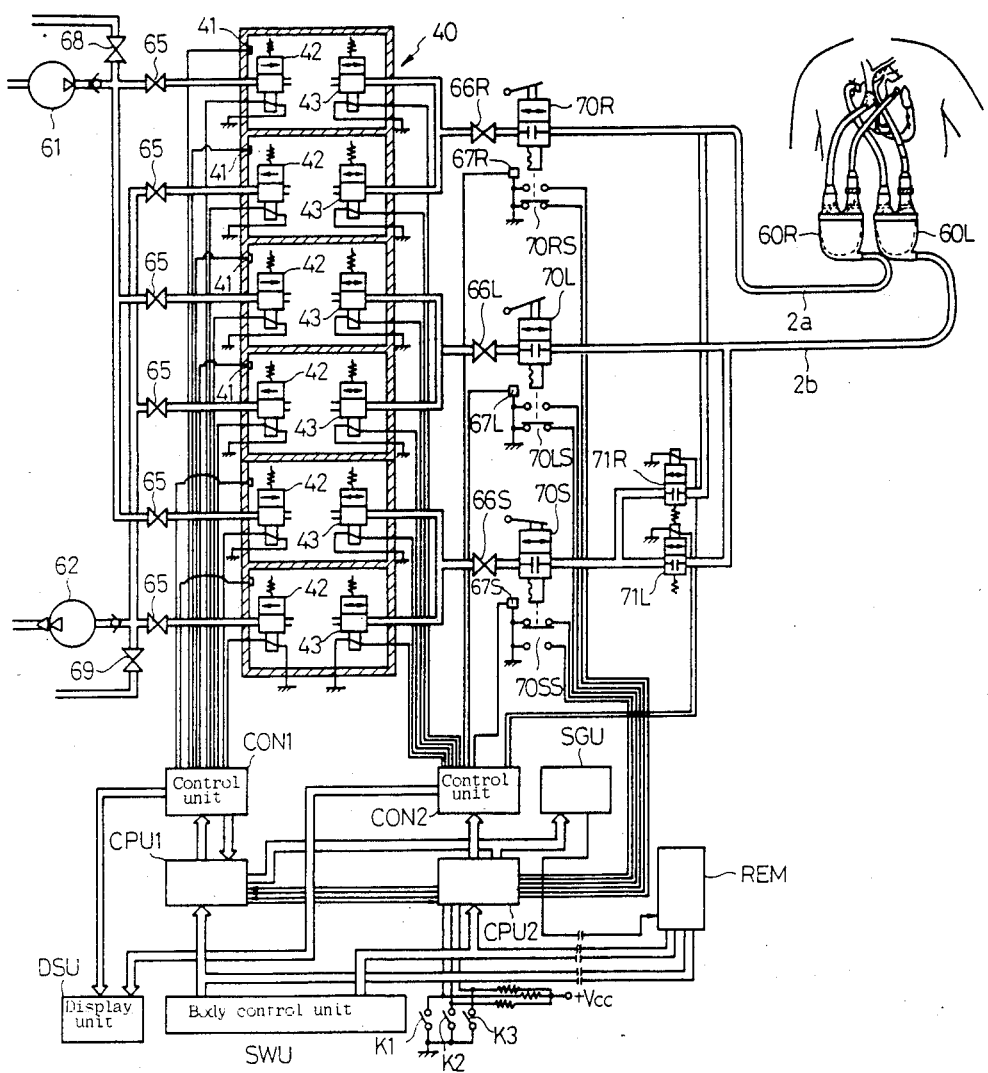
FIG. 20 is a block diagram schematically showing the artificial heart driving apparatus which includes the tank unit illustrated in FIGS. 19a to 19e.

FIG. 20 illustrates schematically the artificial heart driving apparatus together with the artificial hearts. Referring to FIG. 20, designated at 60R and 60L are artificial hearts which are connected to the artificial heart driving apparatus through the tubes 2a and 2b, respectively. These tubes 2a and 2b are connected to the corresponding output terminals of the tank unit 40 through manual selector valves 70R, 70L and cocks 66R, 66L, respectively, while the tubes 2a and 2b are also connected to the output terminals of the backup system through the solenoid valves 71R, 71L, a manual selector valve 70S and a cock 66S. In the vicinity of the manual selector valves 70R, 70L and 70S, there are respectively provided lamps 67R, 67L and 67S. The manual selector valves 70R, 70L and 70S include electric contacts 70RS, 70LS and 70SS which are actuated in accordance with opening and closing of those valves. Designated at 61 is a compressor and 62 is a vacuum pump. Three solenoid valves 42 in the positive pressure systems are connected to the compressor 61 through cocks 65, while three solenoid valves 42 are connected to the vacuum pump 62 through other cocks 65. The reference numerals 68 and 69 denote cocks for connections to a positive pressure source and a negative pressure source in the outside, respectively.

Solenoids of those six solenoid valves 42 and the pressure sensors 41 are connected to the control unit CON1, while solenoids of those six solenoid valves 43 and the solenoid valves 71R, 71L are connected to the control unit CON2. The processing units CPU1 and CPU2 are respectively connected to the control units CON1 and CON2. Control terminals for instructing changes in positive pressure, negative pressure, heart rate and duty ratio are connected to input ports of the processing units CPU1 and CPU2. The control terminals comprise a body control board SWU provided on the control panel 1a of the artificial heart driving apparatus body 1 and a remote control board REM used in remote control. The body control board SWU and the remote control board REM are connected in parallel. A predetermined signal from a sound generating unit SGU is supplied to the remote control board REM. The sound generating unit SGU is controlled by the processing units CPU1 and CPU2. Switches K1, K2 and K3 connected to the processing unit CPU2 are used to instruct switching of the driving systems. The display unit DSU comprises a 7-segment, light emitting diode (LED) indicator or so used for displaying numerals, and it is driven by a digit driving signal and a segment driving signal from both the control units CON1 and CON2 in a dynamic manner.

The microcomputer units CPU1 and CPU2 used in this embodiment has the same structure as that in the foregoing embodiment. Also, the remote control unit REM has the same structure as that in the foregoing embodiment.

Figure 21:
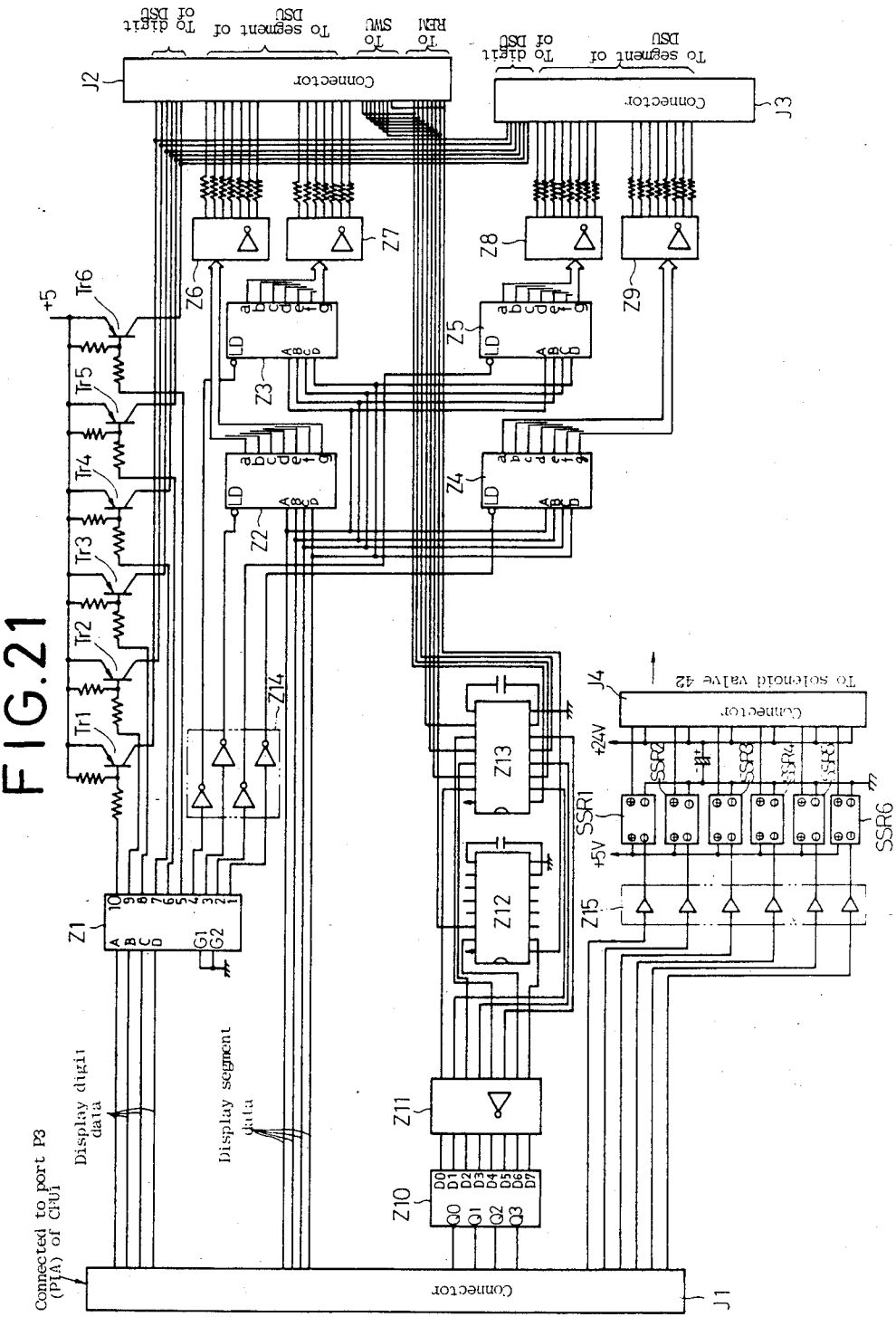
FIG. 21 is a circuit diagram showing a part of a circuitry of the control unit CON1 illustrated in FIG. 20.

FIG. 21 illustrates a part of constitution of the control unit CON1, which further includes the same circuit as that shown in FIG. 13b. The following description will be made by referring to FIG. 21. A connector J1 is connected to an output port P3 of the processing unit CPU1, and for the purpose of displaying in a dynamic driving manner, display data fed from the CPU1 is divided into two BCD signals representing display digit data and display numeral data. The display data output from the CPU1 includes information of positive pressure and negative pressure in both left- and right-hand systems. An integrated circuit Z1 decodes the BCD signal representing the display digit data and then apply thus decoded signals to transistors Tr1 to Tr6 and inverters Z14. The transistors Tr1 to Tr6 are connected to anodes (or digit electrodes) of the light emitting diode type indicator. Integrated circuits Z2 to Z5 serve to convert the BCD signal representing the display numeral data into 7-segment signals, which are applied through drivers Z6 to Z9 to respective cathodes (or segment electrodes) of the light emitting diode type indicator. Key switch contacts of the body control board SWU and key switch contacts of the remote control board REM are connected in parallel in the vicinity of a connector J2, and then they are connected to integrated circuits Z12 and Z13. These integrated circuits Z13 and Z13 include therein a circuit for removing chattering due to the mechanical contacts, thereby to apply signals deprived of such chattering to an integrated circuit Z10 through inverters Z11. The integrated circuit Z10 outputs binary codes in accordance with the key switches pressed down to the microcomputer CPU1 with the preset priority. Designated at SSR1 to SSR6 are solid state relays which are controlled to be on and off with the output port of the microcomputer CPU1 through buffers Z15. Output terminals of the solid state relays SSR1 to SSR6 are connected to the corresponding solenoid valves 42 through a connector J4, respectively.

Referring now to FIG. 13, terminals BIT1 to BIT12 of Z16 serve as signal output terminals, and the terminals BIT1 to BIT4 and the terminals BIT9 to BIT12 are connected to each other. The input port of the microcomputer CPU1 receives a 12-bit signal which is applied thereto in twice by 8 bits at a time. Switching between the terminals BIT1 to BIT4 and the terminals BIT5 to BIT12 is effected in such a manner that the CPU1 controls respective terminals EN1, EN2 and EN3 of the A/D converter Z16. Terminals A1, A2, A4 and A8 are used to select input channels. Although the HDAS-16 has an input port comprising 16 channels, in this embodiment 8 channels among them are connected to a connector J5 and 4 channels among those 8 channels receive signals from the respective pressure sensors 41, that is, a right positive pressure signal RPP, right negative pressure signal RNP, left positive pressure signal LPP and a left negative pressure signal LNP.

Figure 22:
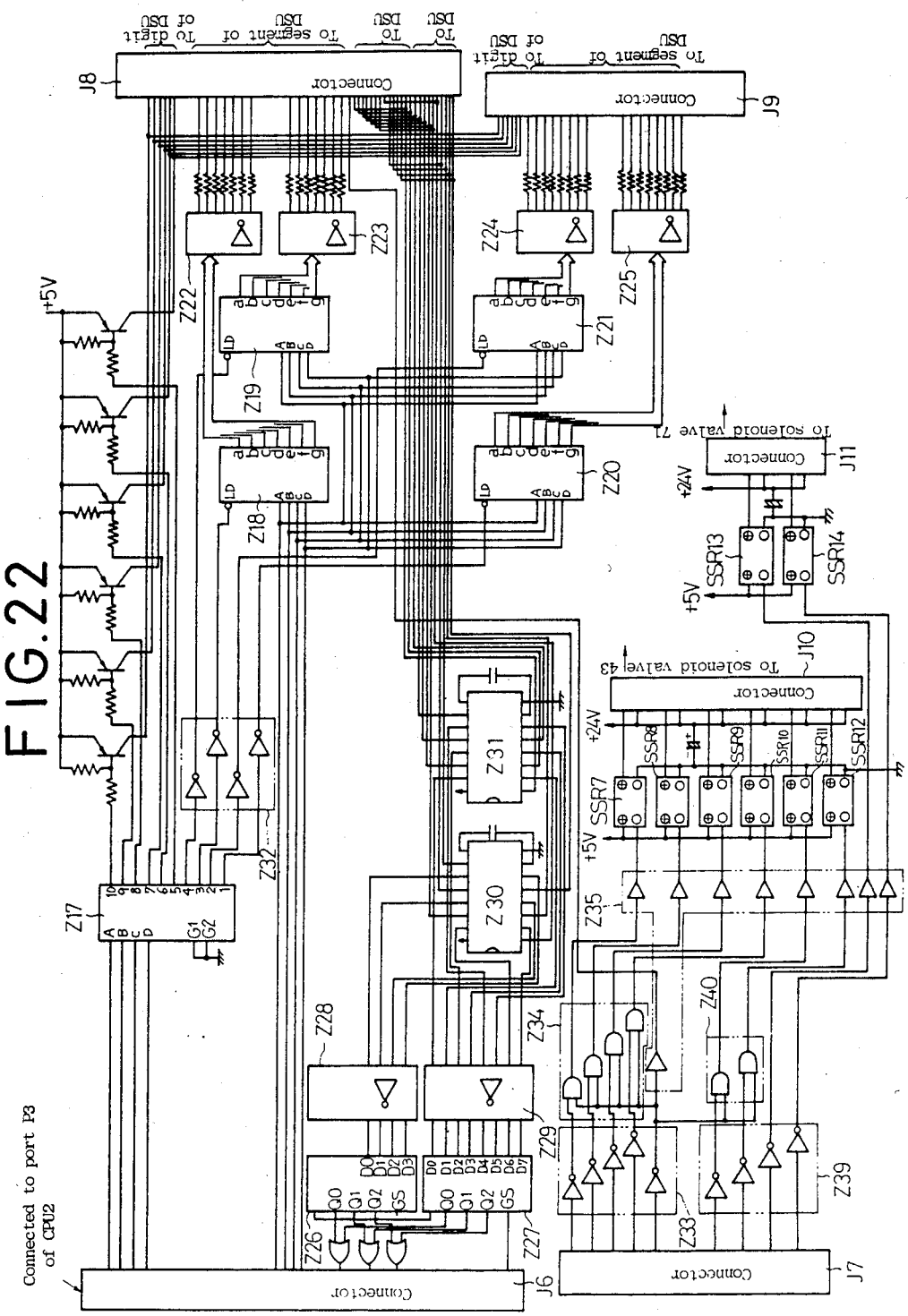
FIG. 22 is a circuit diagram showing a circuitry of the control unit CON2 illustrated in FIG. 20.

FIG. 22 illustrates a circuitry of the control unit CON2. Referring to FIG. 22, the control unit CON2 has a similar structure to that of the aforesaid control unit CON1, but an A/D converter is not included in the control unit CON2 because it has no function to detect pressures. Connectors J6 and J7 are connected to ports P3 and P2 of the processing unit CPU2, respectively. A connector J10 is connected to solenoids of the solenoid valves 43, while a connector J11 is connected to solenoids of the solenoid valves 71R and 71L. To integrated circuits Z30 and Z31 are connected through a connector J8 key switch contacts of the body control board SWU and the remote control board REM, which contacts serve to instruct an increase and a decrease in heart rate, and an increase and a decrease in a ratio of positive pressure applying period and negative pressure applying period for the left- and right-hand artificial hearts, respectively. A connector J11 receives from both CPU1 and CPU2 "ON/OFF" signals which indicates whether the keys are pressed down or not, and also "UP/DOWN" signals which indicate that which one of an increase and a decrease is instructed by the pressed keys.

Since basic operation of the processing unit CPU1 is identical to that of the above-mentioned embodiment shown in FIGS. 16a, 16b and 16c, operation of the CPU1 will be now described by referring to FIGS. 20, 21, 16a, 16b and 16c. The processing unit CPU1 performs reading of key inputs on the body control board SWU or the remote control board REM, reading of respective tank pressures (i.e., outputs of the pressure sensors 41), constant pressure control of the respective tank pressures (i.e., duty control for the solenoid valves 42), changes in the pressure parameters in accordance with key inputs, output of display data, and instruction of generating a sound. Further, control of the solenoid valve 42 in the backup system is carried out not in the normal state, but only when a predetermined signal is input from the processing unit CPU2.

When the power supply comes on, the respective parameters are made to have initial values thereby to set the interrupt enable state. In this embodiment, initial values of RPP, RNP, LPP and LNP are set at +30, −30, +100 and −50 (mmHg), respectively, and upper/lower limits of those pressures are set at +150/0, 0/−100, +300/0 and 0/−150 (mmHg), respectively. Interruption is periodically generated with intervals of 4 ms using a timer within the CPU1. When the interruption occurs, the microprocessor executes the interrupt processing routine as shown in FIG. 16b. In the interrupt processing routine, the A/D converter Z16 is first selected and its input channel is switched in the sequence of CH0, CH1, CH3 and CH4, thereby to perform A/D conversion of the respective tank pressure RPP, RNP, LPP and LNP in turn and then read thus converted digital data. Moreover, "1" or "0" is output to the predetermined ports of P3 to control the solid state relays SSR1 to SSR4, so that four solenoid valves 42 are turned on or off. This on/off switching is carried out in accordance with the duty parameter preset in a memory of the CPU1 in such a manner that the solenoid valves are turned from the on-state to the off-state every n1 times interruptions and are turned from the off-state to the on-state every n2 times interruptions. Thus, a duty ratio of on-state time and off-state time for each solenoid valve 42 is varied along with changes in a value of the parameter. The tank pressure can be held at a predetermined level by controlling such duty ratio in accordance with the result of comparison between the detected pressure and the target pressure for the tank. In the above interrupt processing, the CPU1 always confirms whether the system selective instruction is issued from the CPU2 or not. If there occurs an instruction to drive the backup system, pressures SPP and SNP in the backup system are controlled to be coincident with those in the right- or left-hand system after confirming which one of the right- and left-hand systems should be exchanged. In this case, when both pressures in the backup system reaches the predetermined levels, the CPU1 sends a signal indicating the system switching enable state to the CPU2.

In the tank pressure input subroutine, pressure data of the respective tanks read from the A/D converter Z16 are averaged, and then the data thus averaged are converted into 4-digit, decimal data for display. The reason why the pressure data are averaged is in eliminating minute fluctuations in pressures for a short period of time which are caused upon opening and closing of the valves. When there occurs a key input, it is judged that which key was pressed down and then a value of the parameter corresponding to the pressed key is increased (or decreased) gradually. At the same time, it is also judged that which one of an increase and a decrease is indicated by the pressed key, and then both OFF/ON signal and UP/DOWN signal are applied to the connector J11, so that a given sound is generated from the speaker on the remote control board REM.

Figure 23A:
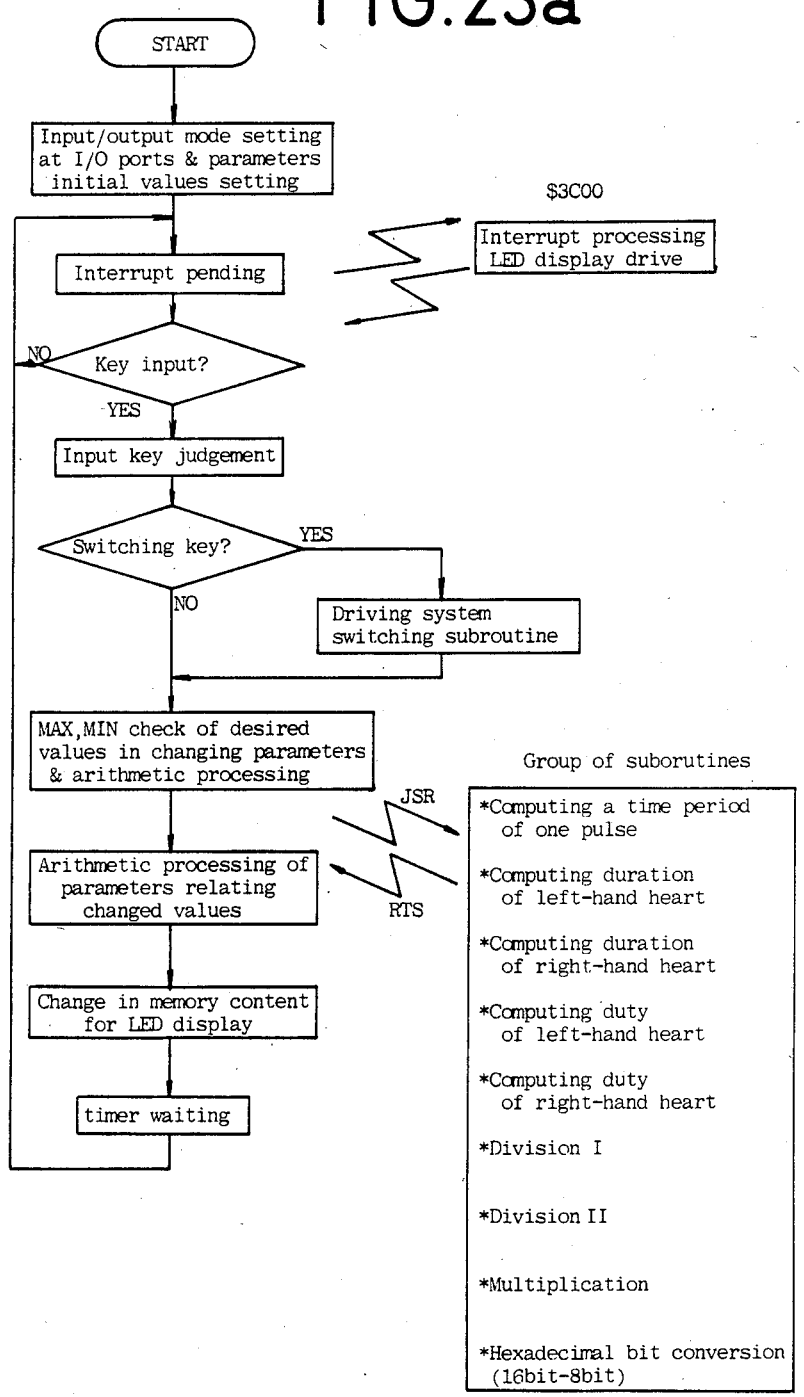

Operation of the processing unit CPU2 will be now described with reference to FIGS. 23a and 23b which show an operation flow thereof schematically. When the power supply comes on, the microprocessor sets first the respective I/O ports at the initial state so that the parameters such as heart rate and a ratio of positive pressure applying time and negative pressure applying time (that is, duty ratio or duration of positive/negative pressure) for the left- and right-hand artificial hearts are made to have their initial values. In this embodiment, the initial values of the respective parameters are set such that heart rate is 100 rpm, a duty ratio of the left-hand artificial heart is 45% (or duration of 270 ms), and a duty ratio of the right-hand artificial heart is 55% (or duration of 330 ms).

In the interrupt processing, a logical level at the predetermined output ports is updated from "1" to "0" or vice versa at certain timing in accordance with the given parameter (i.e., heart rate), thereby to control the solid state relays SSR7 to SSR10 and then open or close the solenoid valves 43. At the same time, output of the display data (comprising digit data and segment data) is effected. When there occurs a key input, it is judged that which key was pressed down, and a value of the parameter corresponding to the pressed key is incremented or decremented during press operation of the key while ocnfirming that its value will not exceed the upper or lower limit. Various parameters relating to that parameter are also subjected to arithmetic processing. This processing is carried out after jumping to the respective subroutines.

A group of subroutines comprises a subroutine for computing a time period of one pulse in terms of heart rate, a subroutine for computing duration of the left-hand artificial heart, a subroutine for computing duration of the right-hand artificial heart, a subroutine for computing a duty ratio of the left-hand artificial heart, a subroutine for computing a duty ratio of the right-hand artificial heart, a subroutine for doing division, a subroutine for doing multiplication and so on. After completion of these calculations, the updated values of the respective parameters are stored in a memory for display and then the flow returns to interrupt standby processing after a predetermined period of time has lapsed. Upon subsequent interruption, the updated data are displayed. When a key input indicates switching of the systems (i.e., the switch K1 is turned on), a driving system switching subroutine will be executed.

Now referring to FIG. 23b, the CPU2 first instructs the CPU1 to control the solenoid valves 42 in the backup system not under operation. Then, a switching sequence starting lamp (not shown) is energized to light up and it waits for a key input which instructs that which one of the right- and left-hand systems is to be switched. Upon instruction of the switched system, the CPU1 starts pressure regulation with the control parameters for the backup system being as the control parameters for the instructed system. The CPU2 waits for completion of that pressure regulation. Thereafter, a lamp 67S provided in the vicinity of the manual valve in the backup system is energized to light up, thereby to inform the operator of that the manual valve 70S in the backup system should be now opened. When the manual valve 70S is opened by the operator, the contact 70SS is actuated so that a signal indicating opening of the valve 70S is applied to the CPU2. Upon opening of the valve 70S, the lamp 67S is turned out, then the solenoid valves 43 in the backup system are operated at the same timing as the solenoid valves 43 in the switched system, and then the solenoid valve 71R or 71L is opened.

In this state, air at the same pressure level is applied from both the switched system and the backup system to the artificial hearts being connected to the former system simultaneously, so that the aritificial hearts are driven by driving sources in parallel. Then, the lamp 67R or 67L near the manual valve in the switched system is energized to light up, thereby to inform the operator of that the manual valve may be closed. Upon closing of the manual valve, the CPU2 instructs the CPU1 to stop operation of the solenoid valves 42 and 43 in the right- or left-hand system. After all of the lamps are turned out, the flow returns to the main processing routine. With this, valves 42, 43, the accumulators, etc. in the instructed system are separated from the aritficial hearts which are now driven by the backup system, so that the separated system may be subject to maintenance or the like. When switching of the driving systems is instructed once again, the separated system is then connected through the sequence opposite to that as mentioned above, while the backup system is separated from the aritificial hearts.

According to this embodiment, it becomes possible to carry out periodical maintenance, system switching and repairs at the time of malfunctioning, etc. in the aritificial heart driving apparatus. In addition, at the time of switching the systems, a possibility of errors caused by operators is minimized so as to ensure a high level of safety.

Having now fully set forth both structure and operation of preferred embodiments of the concept underlying the present invention, various other emobodiments as well as certain variations and modifications of the embodiments herein shown and described will obviously occur to those skilled in the art upon becoming familiar with the underlying concept. It is to be understood, therefore, that with the scope of the appended claims, the invention may be practiced otherwise than as specifically set forth herein.

What we claim is:

1. An artificial heart driving apparatus comprising: a first system including therein; a first solenoid valve having its input port connected to an output port of a positive pressure source; a first accumulator having an inner space connected to an output port of said first solenoid valve; a second solenoid valve having its input port connected to an output port of said first accumulator; a first pressure detecting means for detecting pressure in a fluid path from the output port of said first solenoid valve to the input port of said second solenoid valve; a third solenoid valve having its input port connected to an output port of a negative pressure source; a second accumulator having an inner space connected to an output port of said third solenoid valve; a fourth solenoid valve having its input port connected to an output port of said second accumulator; a second pressure detecting means for detecting pressure in a fluid path from the output port of said third solenoid valve to the input port of said fourth solenoid valve; and an opening and closing valve means having its output port connected to an artificial heart and its input port connected to both the output port of said second solenoid valve and the output port of said fourth solenoid valve;

a second system including therein; a first solenoid valve having its input port connected to an output port of a positive pressure source; a first accumulator having an inner space connected to an output port of said first solenoid valve; a second solenoid valve having its input port connected to an output port of said first accumulator; a first pressure detecting means for detecting pressure in a fluid path from the output port of first solenoid valve to the input port of said second solenoid valve; a third solenoid valve having its input port connected to an output port of a negative pressure source; a second accumulator having an inner space connected to an output port of said third solenoid valve; a fourth solenoid valve having its input port connected to an output port of said second accumulator; a second pressure detecting means for detecting pressure in a fluid path from the output port of said third solenoid valve to the input port of said fourth solenoid valve; and an opening and closing valve means having its output port connected to an artificial heart and its input port connected to both the output port of said second solenoid valve and the output port of said fourth solenoid valve;

a control board;

a change over instructing switch means; and a control unit which controls opening and closing of said first solenoid valve in said first system based on both the pressure detected by said first pressure detecting means in said first system and a first set value preset in accordance with an instruction from said control board, controls opening and closing of said third solenoid valve in said first system based on both the pressure detected by said second pressure detecting means in said first system and a second set value present in accordance with an instruction from said control board, and controls opening and closing of said second solenoid valve and said fourth solenoid valve in said first system at predetermined time intervals, respectively; which upon change over instructions from said change over instructing switch means, controls opening and closing of said first solenoid valve in said second system based on both the pressure detected by said first pressure detecting means in said second system and a first set value preset in accordance with an instruction from said control board, controls opening and closing of said third solenoid valve in said solenoid valve in said second system based on both the pressure detected by said second pressure detecting means in said second system and a second set value preset in accordance with an instruction from said control board and controls opening and closing of said second solenoid valve and said fourth solenoid valve in said second system at the substantially same time intervals as those for said second solenoid valve and said fourth solenoid valve in said first system, respectively.

2. An artificial heart driving apparatus according to claim 1 wherein said opening and closing valve means of said first system and said second system are manual selector valves.

3. An artificial heart driving apparatus according to claim 1, wherein said control board includes a pressure setting instruction means adapted to instruct said first set value and said second set value, a duty setting instruction means adapted to instruct respective ratios of opening time and closing time for said second solenoid valve and said fourth solenoid valve, and a hearbeat period setting instruction means adapted to set respective opening and closing periods of said second solenoid valve and said fourth solenoid valve; and said control unit controls opening and closing of said first solenoid valve to make the detected output from said first pressure detecting means coincident with said first set value, controls opening and closing of said third solenoid valve to make the detected output from said second pressure detecting means coincident with said second set value, and controls said second solenoid valve and said fourth solenoid valve at the preset duty and the preset hearbeat period.

4. An artificial heart driving apparatus according to claim 1 wherein said first system and second system each include an opening and closing signal generating means adapted to output a signal in accordance with the opened and closed state of the respective opening and closing valve means in said first and second system, wherein said control unit stops said control for said first system when said opening and closing signal generating means in said second system indicates opening of said opening and closing valve means in said second system and then said opening and closing signal generating means in said first system indicates closing of said opening and closing valve means in said first system.

5. An artificial heart driving apparatus according to claim 4 wherein said control unit includes a first light emitting means turning operator's attention to said opening and closing valve means of said second system and a second light emitting means turning operator's attention to said opening and closing valve means of said first system, and said control unit adapted to energize said first light emitting means in accordance with a switching instruction from said change over instructing switch means, and to deenergize said first light emitting means and energize said second light emitting means in accordance with a signal indicating opened state of said opening and closing valve means of said second system from said opening and closing signal generating means of said second system.

6. An artificial heart driving apparatus according to claim 4, wherein said opening and closing signal generating means is switch means disposed on said opening and closing valve means.

7. An artificial heart driving apparatus comprising:
  a first system including therein; a first solenoid valve having its input port connected to an output port of a positive pressure source; a first accumulator having an inner space connected to an output port of said first solenoid valve; a second solenoid valve having its input port connected to an output port of said first accumulator; a first pressure detecting means for detecting pressure in a fluid path from the output port of said first solenoid valve to the input port of said second solenoid valve; a third solenoid valve having its input port connected to an output port of a negative pressure source; a second accumulator having an inner space connected to an output port of said third solenoid valve; a fourth solenoid valve having its input port connected to an output port of said second accumulator; a second pressure detecting means for detecting pressure in a fluid path from the output port of said third solenoid valve to the input port of said fourth solenoid valve; and an opening and closing valve means having its output port connected to a first artificial heart and its input port connected to both the output port of said second solenoid valve and the output port of said fourth solenoid valve;
  a second system including therein; a first solenoid valve having its input port connected to an output port of a positive pressure source; a first accumulator having an inner space connected to an output port of said first solenoid valve; a second solenoid valve having its input port connected to an output port of said first accumulator; a first pressure detecting means for detecting pressure in a fluid path from the output port of said first solenoid valve to the input port of said second solenoid valve; a third solenoid valve having its input port connected to an output port of a negative pressure source; a second accumulator having an inner space connected to an output port of said third solenoid valve; a fourth solenoid valve having its input port connected to an output port of said second accumulator; a second pressure detecting means for detecting pressure in a fluid path from the output port of said third solenoid valve to the input port of said fourth solenoid valve; and an opening and closing valve means having its output port connected to a second artificial heart and its input port connected to both the output port of said second solenoid valve and the output port of said fourth solenoid valve;
  a third system including therein; a first solenoid valve having its input port connected to an output port of a positive pressure source; a first accumulator having an inner space connected to an output port of said first solenoid valve; a second solenoid valve having its input port connected to an output port of said first accumulator; a first pressure detecting means for detecting pressure in a fluid path from the output port of said first solenoid valve to the input port of said second solenoid valve, a third solenoid valve having its input port connected to an output port of a negative pressure source; a second accumulator having an inner space connected to an output port of said third solenoid valve; a fourth solenoid valve having its input port connected to an output port of said second accumulator; a second pressure detecting means for detecting pressure in a fluid path from the output port of said third solenoid valve to the input port of said fourth solenoid valve and selector valve means adapted to selectively connect both the output ports of said second solenoid valve means and said fourth solenoid valve means to said first and second artificial hearts;
  a control board;
  a change over instructing switch means; and
  a control unit which controls opening and closing of said first solenoid valve in said first system based on both the pressure detected by said first pressure detecting means in said first system and a first set value preset in accordance with an instruction from said control board, controls opening and closing of said third solenoid valve in said first system based on both the pressure detected by said second pressure detecting means in said first system and a second set value preset in accordance with an instruction from said control board, and controls opening and closing of said second solenoid valve and said fourth solenoid valve in said first system at predetermined time intervals, respectively; which controls opening and closing of said first solenoid valve in said second system based on both the pressure detected by said first pressure detecting means in said second system and a first set value preset in accordance with an instruction from said control board, controls opening and closing of said third solenoid valve in said second system based on both the pressure detected by said second pressure detecting means in said second system and a second set value preset in accordance with an instruction from said control board, and controls opening and closing of said second solenoid valve and said fourth solenoid valve in said second system at predetermined time intervals, respectively; which upon change over instruction from said change over instructing switch means, controls opening and closing of said first solenoid valve in said third system based on both the pressure detected by said first pressure detecting means in said third system and a first set value preset in accordance with an instruction from said control board, controls opening and closing of said third solenoid valve in said third system based on both the pressure detected by said second pressure detecting means in said third system and a second set value preset in accordance with an instruction from said control board, and controls opening and closing of said second solenoid valve and said fourth valve in said third system at the substantially same time intervals as those for said second solenoid valve and said fourth solenoid valve in either one of said first and second systems which was instructed by a switch input, respectively.

8. An artificial heart driving apparatus according to claim 7 wherein said selector valve means are a first opening and closing valve disposed between said first artificial heart and the output ports of said second and fourth solenoid valves of the third system and a second opening and closing valve disposed between said second artificial heart and the output ports of said second and fourth solenoid valves of the third system.

9. An artificial heart driving apparatus according to claim 7 wherein said first system and second system each include an opening and closing signal generating means adapted to output a signal in accordance with the opened and closed state of the respective said opening and closing valve means in said first and second systems.

10. An artificial heart driving apparatus according to claim 7, wherein said opening and closing valve means of said first system and said second system are manual selector valves.

11. An artificial heart driving apparatus according to claim 9 wherein said control unit includes a first light emitting means turning operator's attention to said opening and closing valve means of said second system and a second light emitting means turning operator's attention to said opening and closing valve means of said first system, and said control unit adapted to energize said first light emitting means in accordance with a switching instruction from said change over instructing switch means and to deenergize said first light emitting means and energize said second light emitting means in accordance with signal indicating opened state of said opening said closing valve means of said second system from said opening and closing signal generating means of said second system.

12. An artificial heart driving apparatus according to claim 9 wherein said opening and closing signal generating means is switch means disposed on said opening and closing valve means.

13. An artificial heart driving apparatus according to claim 7, wherein said control board includes a pressure setting instruction means adapted to instruct said first set value and said second set value, a duty setting instruction means adapted to instruct respective ratios of opening time and closing time for said second solenoid valve and said fourth solenoid valve, and a a heartbeat period setting instruction means adapted to set respective opening and closing periods of said second solenoid valve and said fourth solenoid valve; and said control unit controls opening and closing of said first solenoid valve to make the detected output from said first pressure detecting means coincident with said first set value, controls opening and closing of said third solenoid valve to make the detected output from said second pressure detecting means coincident with said second set value, and controls said second solenoid valve and said fourth solenoid valve at the preset duty and the preset heartbeat period.

* * * * *